US009636128B2

(12) United States Patent
Zemlok et al.

(10) Patent No.: US 9,636,128 B2
(45) Date of Patent: May 2, 2017

(54) METHOD AND FORCE-LIMITING HANDLE MECHANISM FOR A SURGICAL INSTRUMENT

(71) Applicant: COVIDIEN LP, Mansfield, MA (US)

(72) Inventors: Michael Zemlok, Prospect, CT (US); Paul A. Scirica, Huntington, CT (US); Robert J. DeSantis, Redding, CT (US)

(73) Assignee: Covidien LP, Mansfield, MA (US)

( * ) Notice: Subject to any disclaimer, the term of this patent is extended or adjusted under 35 U.S.C. 154(b) by 613 days.

(21) Appl. No.: 14/173,220

(22) Filed: Feb. 5, 2014

(65) Prior Publication Data

US 2014/0150600 A1    Jun. 5, 2014

Related U.S. Application Data

(62) Division of application No. 11/543,424, filed on Oct. 5, 2006, now Pat. No. 8,708,210.

(51) Int. Cl.
*A61B 17/068* (2006.01)
*A61B 17/29* (2006.01)
(Continued)

(52) U.S. Cl.
CPC ........ *A61B 17/2909* (2013.01); *A61B 17/068* (2013.01); *A61B 17/10* (2013.01);
(Continued)

(58) Field of Classification Search
CPC .... A61B 17/07207; A61B 2017/07242; A61B 90/03; A61B 17/2909; A61B 2017/2912;
(Continued)

(56) References Cited

U.S. PATENT DOCUMENTS 3,079,606 A    3/1963  Bobrov et al.
3,380,445 A    4/1968  Frasier
(Continued)

FOREIGN PATENT DOCUMENTS

AU    198654765    9/1986
DE    2744824      4/1978
(Continued)

OTHER PUBLICATIONS

Boyles, Walt; "Instrumentation Reference Book", 2002; Butterworth-Heinemann; 262-264.
(Continued)

*Primary Examiner* — Michelle Lopez

(57) ABSTRACT

A safety handle assembly for use with a surgical instrument having an operative distal end portion is disclosed. The handle assembly includes a handle housing and a drive element movably mounted within the handle housing and connected to an associated operative distal end portion. A drive assembly is positioned within the handle housing and is engageable with the drive element to move the drive element within the handle housing. An actuator is movably mounted on the handle housing and an adjustable force-limiting mechanism is interposed between the drive assembly and the actuator. A force-limiting mechanism releasably connects the actuator to the drive assembly. The force-limiting mechanism is adjustable to preset the force at which the actuator separates or breaks away from the drive assembly.

11 Claims, 12 Drawing Sheets

(51) Int. Cl.
*A61B 17/10* (2006.01)
*A61B 90/00* (2016.01)

(52) U.S. Cl.
CPC ......... *A61B 90/03* (2016.02); *A61B 2017/292* (2013.01); *A61B 2017/2912* (2013.01); *A61B 2017/2923* (2013.01); *A61B 2017/2925* (2013.01); *Y10T 74/20612* (2015.01)

(58) Field of Classification Search
CPC ............ A61B 2017/2932; A61B 17/10; A61B 17/068
USPC .................................................... 227/175.1
See application file for complete search history.

(56) References Cited

U.S. PATENT DOCUMENTS

| | | |
|---|---|---|
| 3,490,675 A | 1/1970 | Green et al. |
| 3,534,306 A | 10/1970 | Watrous et al. |
| 3,777,538 A | 12/1973 | Weatherly et al. |
| 4,027,510 A | 6/1977 | Hiltebrandt |
| 4,086,926 A | 5/1978 | Green et al. |
| 4,126,137 A | 11/1978 | Archibald |
| 4,244,372 A | 1/1981 | Kapitanov et al. |
| 4,387,714 A | 6/1983 | Geddes et al. |
| 4,393,584 A | 7/1983 | Bare et al. |
| 4,429,695 A | 2/1984 | Green |
| 4,505,414 A | 3/1985 | Filipi |
| 4,589,413 A | 5/1986 | Malyshev et al. |
| 4,602,634 A | 7/1986 | Barkley |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,658,819 A | 4/1987 | Harris et al. |
| 4,671,445 A | 6/1987 | Barker et al. |
| 4,700,703 A | 10/1987 | Resnick et al. |
| 4,703,887 A | 11/1987 | Clanton et al. |
| 4,725,713 A | 2/1988 | Lehrke |
| 4,728,020 A | 3/1988 | Green et al. |
| 4,752,024 A | 6/1988 | Green et al. |
| 4,784,137 A | 11/1988 | Kulik et al. |
| 4,863,088 A | 9/1989 | Redmond et al. |
| 4,892,244 A | 1/1990 | Fox et al. |
| 4,978,049 A | 12/1990 | Green |
| 4,991,764 A | 2/1991 | Mericle |
| 5,038,796 A | 8/1991 | Axelgaard et al. |
| 5,040,715 A | 8/1991 | Green et al. |
| 5,061,914 A | 10/1991 | Busch et al. |
| 5,065,929 A | 11/1991 | Schulze et al. |
| 5,074,454 A | 12/1991 | Peters |
| 5,083,695 A | 1/1992 | Foslien et al. |
| 5,084,057 A | 1/1992 | Green et al. |
| 5,111,987 A | 5/1992 | Moeinzadeh et al. |
| 5,114,424 A | 5/1992 | Hagen et al. |
| 5,129,570 A | 7/1992 | Schulze et al. |
| 5,141,144 A | 8/1992 | Foslien et al. |
| 5,170,925 A | 12/1992 | Madden et al. |
| 5,171,247 A | 12/1992 | Hughett et al. |
| 5,246,156 A | 9/1993 | Rothfuss et al. |
| 5,271,417 A | 12/1993 | Swanson et al. |
| RE34,519 E | 1/1994 | Fox et al. |
| 5,282,807 A | 2/1994 | Knoepfler |
| 5,286,255 A | 2/1994 | Weber |
| 5,307,976 A | 5/1994 | Olson et al. |
| 5,312,023 A | 5/1994 | Green et al. |
| 5,318,221 A | 6/1994 | Green et al. |
| 5,326,013 A | 7/1994 | Green et al. |
| 5,328,077 A | 7/1994 | Lou |
| 5,332,142 A | 7/1994 | Robinson et al. |
| 5,336,232 A | 8/1994 | Green et al. |
| 5,336,255 A | 8/1994 | Kanare et al. |
| 5,352,315 A | 10/1994 | Carrier et al. |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,376,095 A | 12/1994 | Ortiz |
| 5,381,943 A | 1/1995 | Allen et al. |
| 5,382,255 A | 1/1995 | Castro et al. |
| 5,383,880 A | 1/1995 | Hooven |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,407,293 A | 4/1995 | Crainich |
| 5,413,268 A | 5/1995 | Green et al. |
| 5,415,334 A | 5/1995 | Williamson, IV et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,431,322 A | 7/1995 | Green et al. |
| 5,431,323 A | 7/1995 | Smith et al. |
| 5,433,721 A | 7/1995 | Hooven et al. |
| 5,447,265 A | 9/1995 | Vidal et al. |
| 5,447,513 A | 9/1995 | Davison et al. |
| 5,449,365 A | 9/1995 | Green et al. |
| 5,452,837 A | 9/1995 | Williamson, IV et al. |
| 5,456,401 A | 10/1995 | Green et al. |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Plyley et al. |
| 5,470,010 A | 11/1995 | Rothfuss et al. |
| 5,472,132 A | 12/1995 | Savage et al. |
| 5,474,566 A | 12/1995 | Alesi et al. |
| 5,476,206 A | 12/1995 | Green et al. |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,952 A | 1/1996 | Fontayne |
| 5,486,185 A | 1/1996 | Freitas et al. |
| 5,487,499 A | 1/1996 | Sorrentino et al. |
| 5,487,500 A | 1/1996 | Knodel et al. |
| 5,489,058 A | 2/1996 | Plyley et al. |
| 5,497,933 A | 3/1996 | DeFonzo et al. |
| 5,505,363 A | 4/1996 | Green et al. |
| 5,507,426 A | 4/1996 | Young et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,551,622 A | 9/1996 | Yoon |
| 5,553,765 A | 9/1996 | Knodel et al. |
| 5,554,164 A | 9/1996 | Wilson et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,564,615 A | 10/1996 | Bishop et al. |
| 5,571,116 A | 11/1996 | Bolanos et al. |
| 5,573,543 A | 11/1996 | Akopov et al. |
| 5,575,799 A | 11/1996 | Bolanos et al. |
| 5,577,654 A | 11/1996 | Bishop |
| 5,579,107 A | 11/1996 | Wright et al. |
| 5,584,425 A | 12/1996 | Savage et al. |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |
| 5,599,347 A | 2/1997 | Hart et al. |
| 5,601,224 A | 2/1997 | Bishop et al. |
| 5,601,618 A | 2/1997 | James |
| 5,607,095 A | 3/1997 | Smith et al. |
| 5,615,820 A | 4/1997 | Viola |

(56) References Cited

U.S. PATENT DOCUMENTS

| | | |
|---|---|---|
| 5,618,291 A | 4/1997 | Thompson et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |
| 5,643,319 A | 7/1997 | Green et al. |
| 5,645,209 A | 7/1997 | Green et al. |
| 5,647,526 A | 7/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,680,981 A | 10/1997 | Mililli et al. |
| 5,680,982 A | 10/1997 | Schulze et al. |
| 5,690,269 A | 11/1997 | Bolanos et al. |
| 5,692,668 A | 12/1997 | Schulze et al. |
| 5,697,542 A | 12/1997 | Knodel et al. |
| 5,704,534 A | 1/1998 | Huitema et al. |
| 5,706,997 A | 1/1998 | Green et al. |
| 5,709,334 A | 1/1998 | Sorrentino et al. |
| 5,711,472 A | 1/1998 | Bryan |
| 5,713,505 A | 2/1998 | Huitema |
| 5,716,366 A | 2/1998 | Yates |
| 5,718,719 A | 2/1998 | Clare et al. |
| 5,725,536 A | 3/1998 | Oberlin et al. |
| 5,725,554 A | 3/1998 | Simon et al. |
| 5,728,110 A | 3/1998 | Vidal et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,755,362 A * | 5/1998 | Rodriguez, Jr. .... B05C 17/0123 222/391 |
| 5,762,255 A | 6/1998 | Chrisman et al. |
| 5,762,256 A | 6/1998 | Mastri et al. |
| 5,769,303 A | 6/1998 | Knodel et al. |
| 5,772,673 A | 6/1998 | Cuny et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,834 A | 7/1998 | Lucey et al. |
| 5,797,536 A | 8/1998 | Smith et al. |
| 5,797,537 A | 8/1998 | Oberlin et al. |
| 5,797,538 A | 8/1998 | Heaton et al. |
| 5,810,811 A | 9/1998 | Yates et al. |
| 5,810,855 A | 9/1998 | Rayburn et al. |
| 5,814,055 A | 9/1998 | Knodel et al. |
| 5,816,471 A | 10/1998 | Plyley et al. |
| 5,817,109 A | 10/1998 | McGarry et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Allen et al. |
| 5,833,695 A | 11/1998 | Yoon |
| 5,836,147 A | 11/1998 | Schnipke |
| 5,862,972 A | 1/1999 | Green et al. |
| 5,865,361 A | 2/1999 | Milliman et al. |
| 5,871,135 A | 2/1999 | Williamson IV et al. |
| 5,873,873 A | 2/1999 | Smith et al. |
| 5,897,562 A | 4/1999 | Bolanos et al. |
| 5,901,895 A | 5/1999 | Heaton et al. |
| 5,911,353 A | 6/1999 | Bolanos et al. |
| 5,918,791 A | 7/1999 | Sorrentino et al. |
| 5,919,198 A | 7/1999 | Graves, Jr. et al. |
| 5,922,001 A | 7/1999 | Yoon |
| 5,954,259 A | 9/1999 | Viola et al. |
| 5,980,510 A | 11/1999 | Tsonton et al. |
| 6,004,335 A | 12/1999 | Vaitekunas et al. |
| 6,010,054 A | 1/2000 | Johnson et al. |
| 6,032,849 A | 3/2000 | Mastri et al. |
| 6,050,453 A | 4/2000 | Kelders et al. |
| RE36,720 E | 5/2000 | Green et al. |
| 6,079,606 A | 6/2000 | Milliman et al. |
| 6,086,249 A | 7/2000 | Urich |
| 6,109,500 A | 8/2000 | Alli et al. |
| 6,197,017 B1 | 3/2001 | Brock et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,269,977 B1 | 8/2001 | Moore |
| 6,279,809 B1 | 8/2001 | Nicolo |
| 6,315,183 B1 | 11/2001 | Piraka |
| 6,315,184 B1 | 11/2001 | Whitman |
| 6,325,810 B1 | 12/2001 | Hamilton et al. |
| 6,330,965 B1 | 12/2001 | Milliman et al. |
| 6,357,089 B1 | 3/2002 | Koguchi et al. |
| 6,413,255 B1 | 7/2002 | Stern |
| 6,436,097 B1 | 8/2002 | Nardella |
| 6,439,446 B1 | 8/2002 | Perry et al. |
| 6,443,973 B1 | 9/2002 | Whitman |
| 6,463,623 B2 | 10/2002 | Ahn et al. |
| 6,488,196 B1 | 12/2002 | Fenton, Jr. |
| 6,503,257 B2 | 1/2003 | Grant et al. |
| 6,505,768 B2 | 1/2003 | Whitman |
| 6,544,274 B2 | 4/2003 | Danitz et al. |
| 6,554,844 B2 | 4/2003 | Lee et al. |
| 6,565,554 B1 | 5/2003 | Niemeyer |
| 6,587,750 B2 | 7/2003 | Gerbi et al. |
| 6,592,597 B2 | 7/2003 | Grant et al. |
| 6,594,552 B1 | 7/2003 | Nowlin et al. |
| 6,602,252 B2 | 8/2003 | Mollenauer |
| 6,612,053 B2 | 9/2003 | Liao |
| 6,619,529 B2 | 9/2003 | Green et al. |
| 6,644,532 B2 | 11/2003 | Green et al. |
| 6,656,193 B2 | 12/2003 | Grant et al. |
| 6,669,073 B2 | 12/2003 | Milliman et al. |
| 6,698,643 B2 | 3/2004 | Whitman |
| 6,716,232 B1 | 4/2004 | Vidal et al. |
| 6,722,552 B2 | 4/2004 | Fenton, Jr. |
| 6,731,473 B2 | 5/2004 | Li et al. |
| 6,755,338 B2 | 6/2004 | Hahnen et al. |
| 6,783,524 B2 | 8/2004 | Anderson et al. |
| 6,786,382 B1 | 9/2004 | Hoffman |
| 6,799,063 B2 | 9/2004 | Carson |
| 6,808,262 B2 | 10/2004 | Chapoy et al. |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| RE38,708 E | 3/2005 | Bolanos et al. |
| 6,877,647 B2 | 4/2005 | Green et al. |
| 6,879,880 B2 | 4/2005 | Nowlin et al. |
| 6,889,116 B2 | 5/2005 | Jinno |
| 6,905,057 B2 | 6/2005 | Swayze et al. |
| 6,905,497 B2 | 6/2005 | Truckai et al. |
| 6,953,135 B2 | 10/2005 | Litton et al. |
| 6,953,138 B1 | 10/2005 | Dworak et al. |
| 6,953,139 B2 | 10/2005 | Milliman et al. |
| 6,959,852 B2 | 11/2005 | Shelton et al. |
| 6,964,363 B2 | 11/2005 | Wales et al. |
| 6,978,921 B2 | 12/2005 | Shelton, IV et al. |
| 6,981,628 B2 | 1/2006 | Wales |
| 6,986,451 B1 | 1/2006 | Mastri et al. |
| 6,988,649 B2 | 1/2006 | Shelton, IV et al. |

(56) References Cited

U.S. PATENT DOCUMENTS

| | | |
|---|---|---|
| 6,991,627 B2 | 1/2006 | Madhani et al. |
| 6,997,735 B2 | 2/2006 | Ehr et al. |
| 7,000,818 B2 | 2/2006 | Shelton, IV et al. |
| 7,000,819 B2 | 2/2006 | Swayze et al. |
| 7,025,765 B2 | 4/2006 | Balbierz et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,731 B2 | 6/2006 | Shelton, IV et al. |
| 7,059,508 B2 | 6/2006 | Shelton, IV et al. |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,128,253 B2 | 10/2006 | Mastri et al. |
| 7,128,254 B2 | 10/2006 | Shelton, IV et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,166,102 B2 | 1/2007 | Fleenor et al. |
| 7,223,272 B2 | 5/2007 | Francese et al. |
| 7,258,262 B2 | 8/2007 | Mastri et al. |
| 7,267,675 B2 | 9/2007 | Stern et al. |
| 7,278,562 B2 | 10/2007 | Mastri et al. |
| 7,303,107 B2 | 12/2007 | Milliman et al. |
| 7,308,998 B2 | 12/2007 | Mastri et al. |
| 7,357,287 B2 | 4/2008 | Shelton et al. |
| 7,380,695 B2 | 6/2008 | Doll et al. |
| 7,422,589 B2 | 9/2008 | Newton et al. |
| 7,473,145 B2 | 1/2009 | Ehr et al. |
| 2002/0004498 A1 | 1/2002 | Doherty |
| 2002/0009193 A1 | 1/2002 | Deguchi |
| 2002/0018323 A1 | 2/2002 | Li |
| 2002/0032948 A1 | 3/2002 | Ahn |
| 2002/0036748 A1 | 3/2002 | Chapoy |
| 2002/0045442 A1 | 4/2002 | Silen et al. |
| 2002/0069565 A1 | 6/2002 | Liao |
| 2002/0084304 A1 | 7/2002 | Whitman |
| 2002/0111621 A1 | 8/2002 | Wallace et al. |
| 2002/0143346 A1 | 10/2002 | McGuckin, Jr. et al. |
| 2002/0177843 A1 | 11/2002 | Anderson et al. |
| 2002/0188294 A1 | 12/2002 | Couture |
| 2002/0190093 A1 | 12/2002 | Fenton, Jr. |
| 2003/0009193 A1 | 1/2003 | Corsaro |
| 2003/0105476 A1 | 6/2003 | Sancoff et al. |
| 2003/0132268 A1 | 7/2003 | Whitman |
| 2004/0004105 A1 | 1/2004 | Jankowski |
| 2004/0007608 A1 | 1/2004 | Ehrenfels |
| 2004/0050902 A1 | 3/2004 | Green |
| 2004/0093029 A1 | 5/2004 | Zubik et al. |
| 2004/0094597 A1 | 5/2004 | Whitman |
| 2004/0108357 A1 | 6/2004 | Milliman |
| 2004/0149802 A1 | 8/2004 | Whitman |
| 2004/0150504 A1 | 8/2004 | Nicholson |
| 2004/0173659 A1 | 9/2004 | Green |
| 2004/0199181 A1 | 10/2004 | Knodel et al. |
| 2004/0232199 A1 | 11/2004 | Shelton, IV et al. |
| 2004/0232200 A1 | 11/2004 | Shelton, IV et al. |
| 2004/0232201 A1 | 11/2004 | Wenchell |
| 2004/0243151 A1 | 12/2004 | Demmy |
| 2004/0267310 A1 | 12/2004 | Racenet |
| 2005/0006429 A1 | 1/2005 | Wales |
| 2005/0006430 A1 | 1/2005 | Wales |
| 2005/0006431 A1 | 1/2005 | Shelton, IV et al. |
| 2005/0006432 A1 | 1/2005 | Racenet |
| 2005/0006433 A1 | 1/2005 | Milliman |
| 2005/0006434 A1 | 1/2005 | Wales et al. |
| 2005/0023324 A1 | 2/2005 | Doll et al. |
| 2005/0023325 A1 | 2/2005 | Gresham |
| 2005/0067457 A1 | 3/2005 | Shelton |
| 2005/0067458 A1 | 3/2005 | Swayze et al. |
| 2005/0067459 A1 | 3/2005 | Swayze et al. |
| 2005/0067460 A1 | 3/2005 | Milliman |
| 2005/0072827 A1 | 4/2005 | Mollenauer |
| 2005/0090837 A1 | 4/2005 | Sixto, Jr. et al. |
| 2005/0103819 A1 | 5/2005 | Racenet |
| 2005/0119669 A1 | 6/2005 | Demmy |
| 2005/0127131 A1 | 6/2005 | Mastri |
| 2005/0165415 A1 | 7/2005 | Wales |
| 2005/0173490 A1 | 8/2005 | Shelton, IV |
| 2005/0178813 A1 | 8/2005 | Swayze et al. |
| 2005/0184123 A1 | 8/2005 | Scirica et al. |
| 2005/0184124 A1 | 8/2005 | Scirica et al. |
| 2005/0184125 A1 | 8/2005 | Marczyk |
| 2005/0184126 A1 | 8/2005 | Green et al. |
| 2005/0189397 A1 | 9/2005 | Jankowski |
| 2005/0216055 A1 | 9/2005 | Scirica et al. |
| 2005/0263562 A1 | 12/2005 | Shelton, IV et al. |
| 2005/0279804 A1 | 12/2005 | Scirica et al. |
| 2006/0000867 A1 | 1/2006 | Shelton, IV et al. |
| 2006/0000868 A1 | 1/2006 | Shelton, IV et al. |
| 2006/0011699 A1 | 1/2006 | Olson et al. |
| 2006/0016853 A1 | 1/2006 | Racenet |
| 2006/0022014 A1 | 2/2006 | Shelton, IV et al. |
| 2006/0022015 A1 | 2/2006 | Shelton, IV et al. |
| 2006/0043147 A1 | 3/2006 | Mastri et al. |
| 2006/0049230 A1 | 3/2006 | Shelton, IV et al. |
| 2006/0074411 A1 | 4/2006 | Carmel et al. |
| 2006/0124688 A1 | 6/2006 | Racenet et al. |
| 2006/0151567 A1 | 7/2006 | Roy |
| 2006/0151568 A1 | 7/2006 | Weller et al. |
| 2006/0175375 A1 | 8/2006 | Shelton et al. |
| 2006/0180634 A1 | 8/2006 | Shelton, IV et al. |
| 2006/0201990 A1 | 9/2006 | Mastri et al. |
| 2006/0201991 A1 | 9/2006 | Mastri et al. |
| 2006/0217742 A1 | 9/2006 | Messerly et al. |
| 2006/0226195 A1 | 10/2006 | Scirica et al. |
| 2006/0226196 A1 | 10/2006 | Hueil et al. |
| 2006/0235437 A1 | 10/2006 | Vitali et al. |
| 2006/0255090 A1 | 11/2006 | Milliman et al. |
| 2006/0278680 A1 | 12/2006 | Viola et al. |
| 2006/0278681 A1 | 12/2006 | Viola et al. |
| 2006/0289600 A1 | 12/2006 | Wales et al. |
| 2006/0289602 A1 | 12/2006 | Wales et al. |
| 2007/0045380 A1 | 3/2007 | Mastri et al. |
| 2008/0083806 A1 | 4/2008 | Scirica |
| 2008/0083813 A1 | 4/2008 | Zemlok et al. |
| 2008/0249520 A1 | 10/2008 | Dunning et al. |
| 2008/0249524 A1 | 10/2008 | Dunning |
| 2008/0281309 A1 | 11/2008 | Dunning et al. |
| 2008/0281310 A1 | 11/2008 | Dunning et al. |
| 2008/0281311 A1 | 11/2008 | Dunning et al. |
| 2009/0036884 A1 | 2/2009 | Gregg et al. |
| 2009/0036885 A1 | 2/2009 | Gregg |

FOREIGN PATENT DOCUMENTS

| | | |
|---|---|---|
| DE | 2903159 | 1/1980 |
| DE | 3114135 | 10/1982 |
| DE | 3206947 | 9/1983 |
| DE | 3544443 | 6/1987 |
| DE | 4213426 | 10/1992 |
| DE | 4231236 | 3/1994 |
| DE | 4300307 | 7/1994 |
| DE | 10328514 | 3/2005 |
| DE | 102004010940 | 9/2005 |
| EP | 0041022 | 12/1981 |
| EP | 0136950 | 4/1985 |
| EP | 0140552 | 5/1985 |
| EP | 0156774 | 10/1985 |
| EP | 0216532 | 4/1987 |
| EP | 0220029 | 4/1987 |
| EP | 0213817 | 11/1987 |
| EP | 0262888 | 4/1988 |
| EP | 0273468 | 7/1988 |
| EP | 0324166 | 7/1989 |
| EP | 0324635 | 7/1989 |
| EP | 0324637 | 7/1989 |
| EP | 0324638 | 7/1989 |
| EP | 0369324 | 5/1990 |

(56) References Cited

FOREIGN PATENT DOCUMENTS

| | | |
|---|---|---|
| EP | 0373762 | 6/1990 |
| EP | 0380025 | 8/1990 |
| EP | 0399701 | 11/1990 |
| EP | 0449394 | 10/1991 |
| EP | 0484677 | 5/1992 |
| EP | 0489436 | 6/1992 |
| EP | 0503662 | 9/1992 |
| EP | 0514139 | 11/1992 |
| EP | 0536903 | 4/1993 |
| EP | 0537572 | 4/1993 |
| EP | 0539762 | 5/1993 |
| EP | 0545029 | 6/1993 |
| EP | 0552050 | 7/1993 |
| EP | 0552423 | 7/1993 |
| EP | 0579038 | 1/1994 |
| EP | 0589306 | 3/1994 |
| EP | 0591946 | 4/1994 |
| EP | 0592243 | 4/1994 |
| EP | 0593920 | 4/1994 |
| EP | 0598202 | 5/1994 |
| EP | 0598579 | 5/1994 |
| EP | 0621006 | 10/1994 |
| EP | 0621009 | 10/1994 |
| EP | 0656188 | 6/1995 |
| EP | 0365153 | 8/1995 |
| EP | 0666057 | 8/1995 |
| EP | 0705571 | 4/1996 |
| EP | 0930048 | 7/1999 |
| EP | 1076350 | 2/2001 |
| EP | 1468653 | 10/2004 |
| EP | 1645236 | 4/2006 |
| EP | 1707151 | 10/2006 |
| EP | 1808144 | 7/2007 |
| EP | 1902684 | 3/2008 |
| FR | 2516782 | 5/1983 |
| FR | 2542188 | 9/1984 |
| FR | 2660851 | 10/1991 |
| FR | 2681775 | 10/1991 |
| GB | 1352554 | 4/1971 |
| GB | 1452185 | 10/1976 |
| GB | 1555455 | 11/1979 |
| GB | 2048685 | 12/1980 |
| GB | 2054382 | 2/1981 |
| GB | 2070499 | 9/1981 |
| GB | 2141066 | 12/1984 |
| GB | 2165559 | 4/1986 |
| GB | 2374532 | 10/2002 |
| JP | 51-149985 | 5/1975 |
| SU | 728848 | 5/1977 |
| SU | 659146 | 4/1979 |
| SU | 980703 | 12/1982 |
| SU | 990220 | 1/1983 |
| WO | WO 83/02247 | 7/1983 |
| WO | WO 89/10094 | 11/1989 |
| WO | WO 92/10976 | 7/1992 |
| WO | WO 93/08754 | 5/1993 |
| WO | WO 93/14706 | 8/1993 |
| WO | WO 96/19152 | 6/1996 |
| WO | WO 00/06246 | 2/2000 |
| WO | WO 2005/087124 | 9/2005 |
| WO | WO 2005/099606 | 10/2005 |
| WO | WO 2005/115262 | 12/2005 |
| WO | WO 2008/009385 | 1/2008 |

OTHER PUBLICATIONS

International Search Report EP 07253835.8 dated Feb. 20, 2007.
European Search Report for EP 07253835.8-2318 completed Nov. 28, 2007; (6 pages).
International Search Report EP 07018375.1 dated Jan. 8, 2008.
International Search Report EP 07019173.9 dated Feb. 12, 2008.
International Search Report EP 07019178.8 dated Feb. 12, 2008.
International Search Report EP 06023756.7 dated Feb. 21, 2008.
International Search Report EP 08006731 dated Jul. 14, 2008.
International Search Report EP 08006731.7 dated Jul. 29, 2008.
International Search Report EP 08006734.1 dated Aug. 18, 2008.
International Search Report EP 08155779—partial dated Sep. 8, 2008.
International Search Report EP 08008510.3 dated Oct. 27, 2008.
International Search Report EP 08013758.1 dated Nov. 20, 2008.
International Search Report EP 08013760.7 dated Nov. 20, 2008.
International Search Report EP 07000567.3 dated Dec. 3, 2008.
International Search Report EP 08006735.8 dated Jan. 8, 2009.
International Search Report EP 08155779 dated Jan. 23, 2009.
International Search Report EP 09152130.2 dated Apr. 6, 2009.
International Search Report EP 09152032 dated Jun. 17, 2009.

* cited by examiner

METHOD AND FORCE-LIMITING HANDLE MECHANISM FOR A SURGICAL INSTRUMENT

CROSS-REFERENCE TO RELATED APPLICATION

The present application is a Divisional Application claiming the benefit of and priority to U.S. patent application Ser. No. 11/543,424, filed on Oct. 5, 2006, the entire content of which is incorporated herein by reference.

BACKGROUND

Technical Field

The present disclosure relates to a method and handle assembly for use with a surgical instrument. More particularly, the present disclosure relates to a method and handle assembly incorporating a force-limiting handle mechanism for use with a surgical instrument having a distal end effector.

Background of Related Art

Various instruments are used during surgical procedures to manipulate tissue. Some of these instruments incorporate a handle assembly which is provided to transmit a force to an end effector applied to tissue. For example, some surgical instruments may be provided with a pair of jaws on the distal end to grasp or cut various tissues. Operation of the handle assembly opens and closes the jaws by transmitting a force from a trigger mechanism associated with the handle assembly to the jaws and thus to the tissue. Other types of surgical instruments may be provided with fastener applying end effectors which are configured to apply staples, clips, or other fasteners to tissue. Operation of the handle assemblies associated with these types of surgical instruments functions to drive staples through and/or into tissue or compress surgical clips about the tissue by transmitting a force from the handle assembly to the staple or clip applying end effector.

During the performance of certain surgical procedures with the above described surgical instruments, application and transmission of force from the handle assemblies to the end effectors may ultimately result in excessive damage to the tissues being operated on. For example, when grasping instruments are utilized to manipulate tissue, excessive force applied to tissue may inadvertently cause damage to tissue.

In addition to the potential for damaging tissue due to excessive force transmitted from the handle assembly to the end effector of a surgical instrument, damage may also occur to the instrument itself. This may occur where the tissue being operated on is sufficiently stiff or hard such that it cannot be compressed or cut by the surgical instrument. Additionally, certain hard tissues may not be able to be penetrated by the amount of force applied to fasteners in situations where stapling of tissue is desired. Similarly, instruments may not be able to completely compress the tissues where compression of tissues is required during the application of surgical clips. Furthermore, many surgical instruments utilize replaceable or disposable cartridge assemblies to apply multiple clips or staples to tissue. Improper positioning of the cartridge assemblies on the surgical instrument, or malfunction of the cartridge assemblies themselves, may result in a resistance of the surgical instrument to application of pressure on the trigger of a handle assembly thereby causing damage to the surgical instrument itself. This may also occur where the cartridge assembly is devoid of fasteners and the surgeon attempts to continue or reuse the surgical instrument.

Thus, a handle assembly for use with a surgical instrument which incorporates a mechanism to limit the amount of force transmitted from the handle assembly to the end effectors to prevent damage to tissue may be useful. Furthermore, a handle assembly for use with a surgical instrument which is capable of limiting the amount of force transmitted to an end effector to prevent damage to the surgical instrument itself may also be useful.

SUMMARY

There is disclosed a handle assembly having an adjustable force-limiting mechanism for use with a surgical instrument having an operative distal end portion. The handle assembly generally includes a handle housing and a drive element movably mounted within the handle housing and connected to an operative distal end portion. A drive assembly is positioned within the handle housing and is engageable with the drive element to move the drive element within the handle housing. An actuator is movably mounted on the handle housing.

A force-limiting mechanism is interposed between the drive assembly and the actuator such that the force-limiting mechanism releasably connects the actuator to the drive assembly. The force-limiting mechanism includes a connecting rod having a first end attached to the drive assembly and a second end mounted within the actuator. The force-limiting mechanism includes a spring positioned within the actuator and adjacent the second end of the connecting rod. The force-limiting mechanism also includes an adjustment screw positioned within the actuator and engageable with the spring to vary the force within the spring.

The connecting rod has a protrusion and the drive assembly includes a cut out portion releasably engageable with the protrusion on the connecting rod. In one embodiment, the drive assembly includes an upper carrier and a lower carrier. The upper carrier is connected to a first end of the connecting rod. The lower carrier includes the cut out portion of the drive assembly and is engageable with the protrusion on the connecting rod. In one embodiment, the connecting rod has a ramp for supporting the portion of the lower carrier including the cut out portion when the cut out portion is disengaged from the protrusions on the connecting rod.

The lower carrier is rotatably mounted on the handle housing and defines a first axis with a pivot point on the upper carrier. The connecting rod defines a second axis with a connection point on the upper carrier. The first and second axes are substantially parallel when the protrusions are engaged with the cut outs. The first and second axes are substantially nonparallel when the protrusions are disengaged from the cut outs. In one embodiment, the lower carrier has at least one flexible arm containing the cut out. The flexible armed is flexible outwardly relative to the lower carrier when the protrusion is disengaged from the cut out to disconnect the drive assembly from the connecting rod. The connecting rod includes a ramp for support of the flexible arm when the protrusion is disconnected from the cut out.

There is also disclosed a handle assembly for use with a surgical instrument having an operative distal end portion. The handle assembly generally includes a handle housing and a rack movably mounted within the handle housing and connected to an operative distal end portion. A drive assembly is positioned within the handle housing and includes a pawl engageable with the rack. A trigger is pivotally mounted on the handle housing and an adjustable force-limiting mechanism is releasably attached to a portion of the drive assembly. A portion of the adjustable force-limiting mechanism is mounted for movement within the trigger. The adjustable force-limiting mechanism releasably connects the trigger to the drive assembly.

The adjustable force-limiting mechanism includes a connecting rod having a first end connected to a portion of the drive assembly and a second end movably mounted within the trigger. The adjustable force-limiting mechanism also includes a spring mounted within the trigger such that the first end of the spring is engageable with the second end of the connecting rod. An adjustment screw is mounted within the trigger such that rotation of the adjustment screw alters the pressure within the spring. In one embodiment, the adjustable force-limiting mechanism includes a bushing mounted within the trigger and positioned between the spring and the adjustment screw.

In an embodiment, the force-limiting mechanism includes a carriage attached to the actuator. It is envisioned that the handle assembly includes a pawl pivotably connected to the carriage. The force-limiting mechanism includes a plunger slidably connected to the actuator. The plunger is slidably disposed at least partially in the actuator. In an embodiment, at least one spring is disposed between the plunger and the actuator. It is envisioned that the carriage has an angled surface for engaging the plunger. The plunger has an angled face for engaging the angled surface of the carriage. The angled surface and the angled face are arranged so that the carriage depresses the plunger. The plunger is biased toward the carriage with a predetermined biasing force.

There is also disclosed a method of controlling the amount of force applied to an end effector by handle assembly which includes providing a handle assembly having a handle housing and a rack movably mounted within the handle housing. A drive assembly is mounted within the handle housing and is engageable with a rack. A trigger is pivotally mounted within the handle housing and a force-limiting mechanism is interposed between the drive assembly and the trigger such that the force-limiting mechanism releasably connects the trigger to the drive assembly. At least a portion of the force-limiting mechanism is urged into engagement with the drive assembly by a predetermined force. The force-limiting mechanism is released from the drive assembly in response to a predetermined amount of force applied to the rack. The portion of the force-limiting mechanism urged into engagement with the drive assembly includes a spring biased plunger which is configured to engage the drive assembly.

DESCRIPTION OF THE DRAWINGS

An embodiment of the presently disclosed handle assembly incorporating an adjustable force-limiting mechanism is disclosed herein with reference to the drawings, wherein.

DETAILED DESCRIPTION OF EMBODIMENTS

An embodiment of the presently disclosed handle assembly incorporating a force-limiting handle mechanism will now be described in detail with reference to the drawings wherein like numerals designate identical or corresponding elements in each of the several views. As is common in the art, the term "proximal" refers to that part or component closer to the user or operator, e.g., surgeon or physician, while the term "distal" refers to that part or component farther away from the user.

Figure 1:
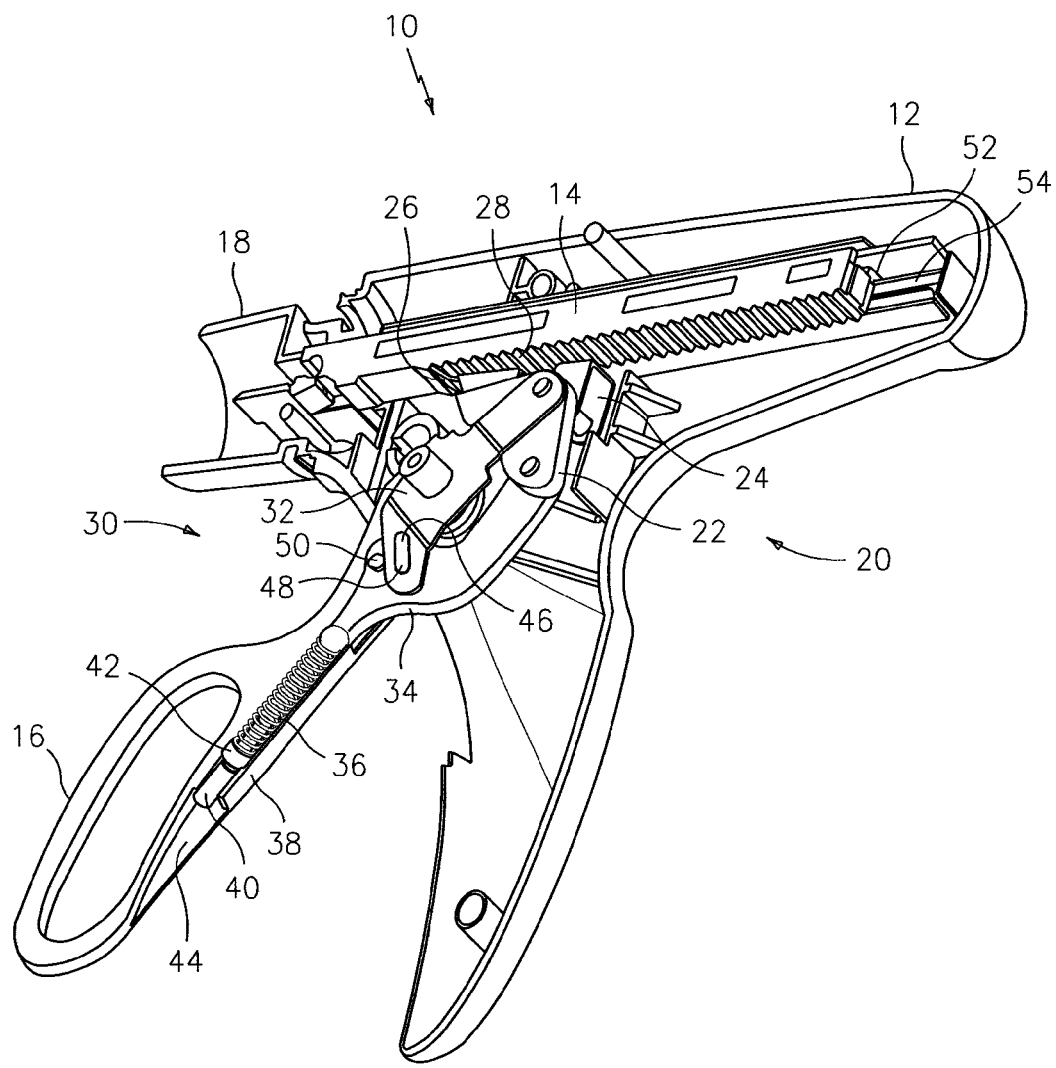
FIG. 1 is a perspective view of the handle assembly with half of a handle housing removed.

Referring initially to FIG. 1, there is disclosed a handle assembly 10 for use with a surgical instrument. Handle assembly 10 incorporates an adjustable force-limiting mechanism 30 (e.g., clutch) to prevent excessive force applied to tissue and to prevent damage to handle assembly 10 itself in the event of an overload condition present at an associated end effector. Handle assembly 10 is particularly suitable for use in surgical instruments incorporating end effectors, such as clip or staple applying apparatus, in their distal end portions. Handle assembly 10 generally includes a handle housing 12 having an elongate driving rack 14 mounted for longitudinal movement within handle housing 12. While handle assembly 10 is illustrated with only one half of handle housing 12 visible, a complete and fully functional handle assembly 10 includes two halves of handle housing 12. Handle assembly 10 additionally includes an actuator or trigger 16 movably mounted on handle housing 12. Actuation of trigger 16 causes driving rack 14 to move longitudinally within handle housing 12.

Handle housing 12 is additionally provided with a journaled nose portion 18 for rotatable support of the distal end portion of a surgical instrument. This allows end effectors associated with the distal end portion of the surgical instrument to be rotated relative to handle assembly 10.

To move driving rack 14, handle assembly 10 includes a drive assembly 20 positioned between driving rack 14 and trigger 16. Drive assembly 20 transfers motion applied to trigger 16 by a portion of an operator's hand to driving rack 14 to translate driving rack 14 longitudinally within handle housing 12 and thus actuate an associated end effector. Drive assembly 20 includes an upper carrier 22 and a pawl 24 for moving rack 14 within handle housing 12 in response to actuation of trigger 16 in a manner described in more detail hereinbelow. Specifically, pawl 24 is provided with a distal lip 26 which is configured to engage teeth 28 formed in rack 14. Teeth 28 are oriented such that distal lip 26 can engage teeth 28 and move driving rack 14 distally within handle housing 12 when pawl 24 is moved in the distal direction and disengage from driving rack 14 as pawl 24 is drawn in a proximal direction relative to driving rack 14.

As noted hereinabove, handle assembly 10 includes adjustable force-limiting mechanism 30 which is provided to disengage trigger 16 from drive assembly 20, and thus from driving rack 14, when force-limiting mechanism 30 encounters a predetermined amount of force between drive assembly 20 and trigger 16. This may occur in a situation where an end effector encounters sufficiently stiff or tough materials such that continued actuation of the surgical instrument results in damage to the surgical instrument or tissues. Additionally, the excessive force condition may occur in the event of damage to the associated end effectors thereby preventing driving rack 14 from translating longitudinally within handle housing 12.

In a particular application, the limit of the excessive force condition may be preset during configuration of handle assembly 10 such that an end effector associated with handle assembly 10 may only apply a force up to a predetermined force to the tissue being operated upon. This may be desirable when the associated end effector is configured to apply surgical clips or staples to tissue. Once the predetermined or preset force has been reached, force-limiting mechanism 30 enables trigger 16 to be disengaged from drive assembly 20 thereby preventing an excess of amount of force being applied to the tissues.

Force-limiting mechanism 30 generally includes a lower carrier 32, which also forms a part of drive assembly 20, and a connecting rod 34 engageable with lower carrier 32 and upper carrier 22. Adjustable force-limiting mechanism 30 additionally includes a pressure spring 36 positioned within a pocket 38 in trigger 16. In an embodiment, pressure spring 36 supplies a progressive force bias to trigger 16 when force-limiting mechanism 30 is engaged to limit or prevent a large force disparity and/or acceleration of trigger 16 to its user. Pressure spring 36 also applies pressure to connecting rod 34 and is adjustable by means of an adjustment screw 40 located within trigger 16. A bushing 42 is also positioned within trigger 16 to support pressure spring 36 within trigger pocket 38. Bushing 42 has a threaded interior for receipt of adjustment screw 40 such that rotation of adjustment screw 40 moves bushing 42 to increase or decrease the pressure in pressure spring 36. Trigger 16 may include a window 44 for remote access to adjustment screw 40 to adjust the pressure applied by pressure spring 36 on connecting rod 34.

As noted above, lower carrier 32 forms a portion of both drive assembly 20 and adjustable force-limiting mechanism 30. Lower carrier 32 allows drive assembly 20 to be disconnected from connecting rod 34 and thus from trigger 16. Lower carrier 32 includes one or more cut outs 46 which cooperate with corresponding one or more protrusions 48 formed on connecting rod 34 to maintain lower carrier 32 in engagement with connecting rod 34. During an excessive pressure condition, cut outs 46 allow lower carrier 32 to disengage from connecting rod 34 by flaring outwardly away from protrusions 48 in a manner described in more detail hereinbelow. Ramps 50 are provided on connecting rod 34 to maintain lower carrier 32 in a flared or splayed condition after carrier 32 has been released from connecting rod 34. By maintaining lower carrier 32 in the flared condition, carrier 32 can reengage connecting rod 34. Additionally, ramps 50 facilitate reengagement of protrusion 48 into carrier 32 when trigger 16 is at least partially released.

As discussed, rack 14 is mounted for longitudinal movement within handle housing 12. Rack 14 includes a rack lip 52 which rides along a housing rail 54 formed in handle housing 12.

Figure 2:
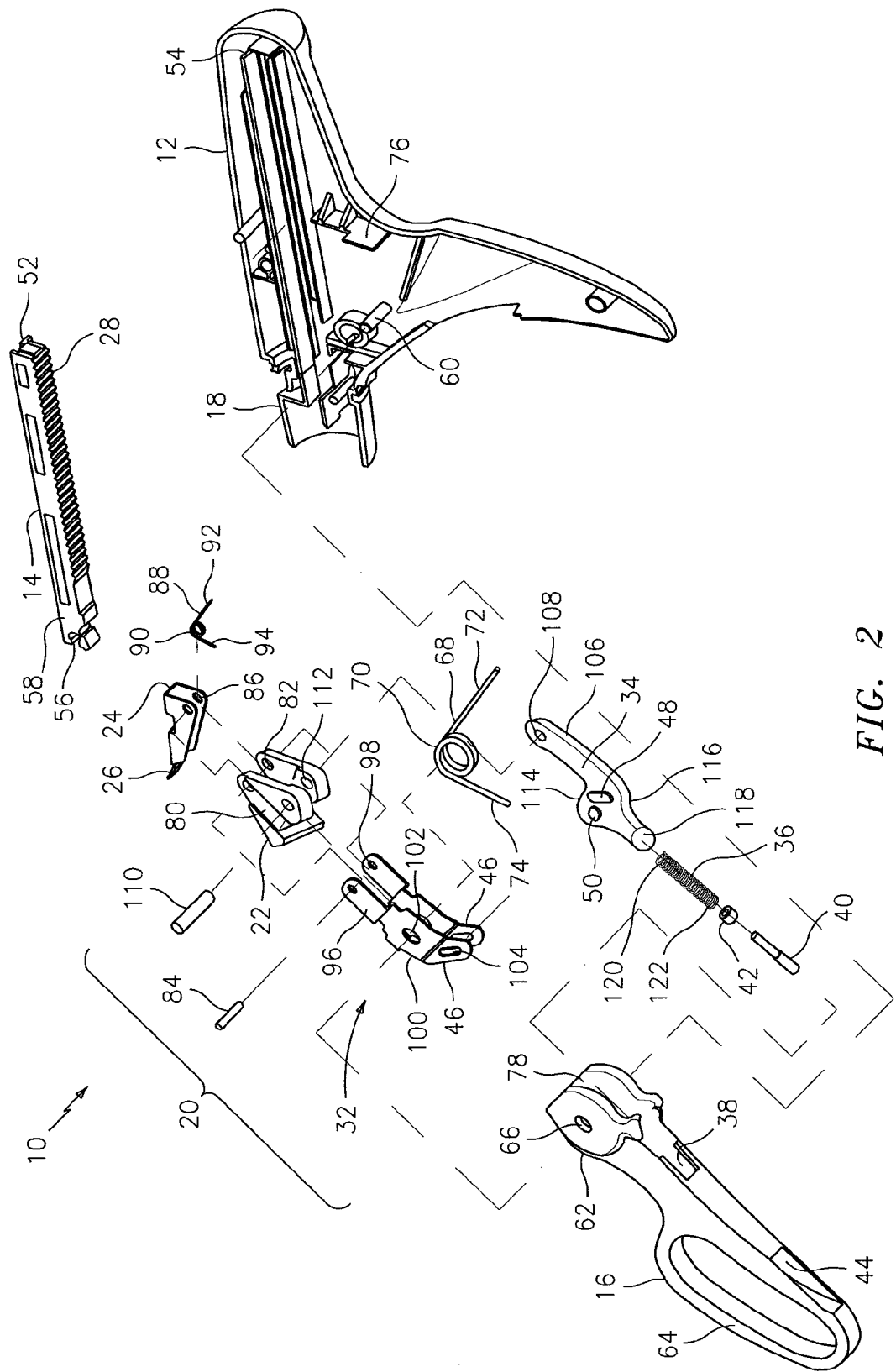
FIG. 2 is a perspective view of the handle assembly with the parts separated.

Referring now to FIG. 2, handle assembly 10 is configured for use with surgical instruments, especially those of the type having an elongate distal end incorporating moving end effectors. For example, handle assembly 10 is particularly suitable for use with clip or staple applying surgical instruments. The inclusion of adjustable force-limiting mechanism 30 in handle assembly 10 allows the operator to preset the maximum amount of force that can be applied by the end effectors to a surgical clip or staple and/or to the tissue being compressed. Typical clip applying apparatus include drive rods which transfer motion from handle assembly 10 to end effectors or jaws of the clip applying surgical instrument. To accommodate the drive rod, rack 14 of handle assembly 10 includes a socket 56 formed in a distal end 58 of rack 14. Socket 56 allows rack 14 to be connected to a drive rod such that rack 14 can move the drive rod longitudinally within an associated distal end portion of a surgical instrument. Socket 56 also allows the drive rod to rotate within socket 56 as the distal end portion of the surgical instrument is rotated relative to handle assembly 10.

To mount trigger 16 to handle assembly 12, handle assembly 12 is provided with a mounting post 60. Trigger 16 includes a body portion 62 and a finger grip portion 64 depending from body portion 62. Body portion 62 includes a pivot hole 66 which fits over mounting post 60 and allows trigger 16 to pivot relative to handle housing 12. A torsion spring 68 is provided to bias trigger 16 to an open position relative to handle housing 12. Torsion spring 68 includes a central portion 70, a first arm 72 and a second arm 74. Central portion 70 fits within body portion 62 of trigger 16 and over mounting post 60. First arm 72 of torsion spring 68 engages a housing wall 76 formed on handle housing 12 while second arm 74 engages an internal surface 78 of body portion 62.

As noted hereinabove, drive assembly 20 generally includes upper carrier 22, pawl 24 and lower carrier 32. Upper carrier 22 includes a pair of grooves or slots 80 for receipt of a portion of lower carrier 32. Pin holes 82 are provided in upper carrier 22 for receipt of a pin 84 to connect upper carrier 22 to pawl 24 as well as to secure upper carrier 22 to lower carrier 32. Pawl 24 includes a pair of pivot holes 86 for receipt of pin 84 to pivotally connect pawl 24 to upper carrier 22. To bias pawl 24 upwardly into engagement with rack 14, drive assembly 20 includes a torsion spring 88. Torsion spring 88 includes a central portion 90, a first arm 92 and a second arm 94. Central portion 90 fits between pivot holes 86 and mounts over pin 84. First arm 92 engages an inside surface of pawl 24 (not shown) while second arm 94 engages an inner surface of upper carrier 22 (not shown).

Lower carrier 32 is formed as a generally U-shaped member and includes a pair of upper arms 96 which fits within slots 80 in upper carrier 22. Upper arms 96 include mounting holes 98 which align with pin holes 82 in upper carrier 22 for receipt of pin 84 to secure lower carrier 32 to upper carrier 22. Lower carrier 32 additionally includes a central portion 100 having pivot holes 102 which are provided to rotatably mount lower carrier 32 on mounting post 60. When assembled, lower carrier 32 fits within body portion 62 of trigger 16 such that torsion spring 68 is positioned between mounting holes 102 in lower carrier 32. Lower carrier 32 incorporates a pair of cut outs 46 which are configured to fit over protrusions 48 on connecting rod 34. Cut outs 46 are formed in lower arms 104 of lower carrier 32. It should be noted that lower arms 104 may be sufficiently flexible relative to central portion 100 and connecting rod 34 such that lower arms 104 can flex or splay outwardly to clear cut outs 46 over protrusions 48 in connecting rod 34. In this manner, lower arms 104 are disconnected from connecting rod 34 when handle assembly 10 encounters the excessive force conditions noted above.

Handle assembly 10 includes force-limiting mechanism 30 which is able to disconnect trigger 16 from drive assembly 20 during the presence of an excessive force condition. Force-limiting mechanism 30 is adjustable so that the operator can preset the exact amount of force, the "break away force," which will cause trigger 16 to be disconnected from drive assembly 20. Adjustable force-limiting mechanism 30 generally includes connecting rod 34, spring 36, as well as, bushing 42 and adjustment screw 40. Connecting rod 34 includes an upper arm 106 having a pivot hole 108 for receipt of a pin 110. Pin 110 connects upper arm 106 of connecting rod 34 to upper carrier 22. Specifically, upper carrier 22 includes a pair of mounting holes 112 for receipt of pin 110 to pivotally connect upper carrier 22 with connecting rod 34.

Connecting rod 34 includes a central portion 114 upon which are located at least one protrusion 48, as well as at least one ramp 50, which can connect and disconnect connecting rod 34 to lower carrier 32 in a manner described in more detail hereinbelow. Connecting rod 34 additionally includes a lower arm 116 which terminates in a ball end 118. A portion of lower arm 116 and ball end 118 extends into pocket 38 formed in trigger 16 such that connecting rod 34 is constrained from movement within pocket 38. Ball end 118 is configured to rest against a first end 120 of spring 36 such that spring 36 provides upward pressure to connecting rod 34. A second end 122 of spring 36 is configured to receive bushing 42 as well as adjustment screw 40. Rotation of adjustment screw 40 causes bushing 42 to increase or decrease the compression within spring 36.

Figure 3:
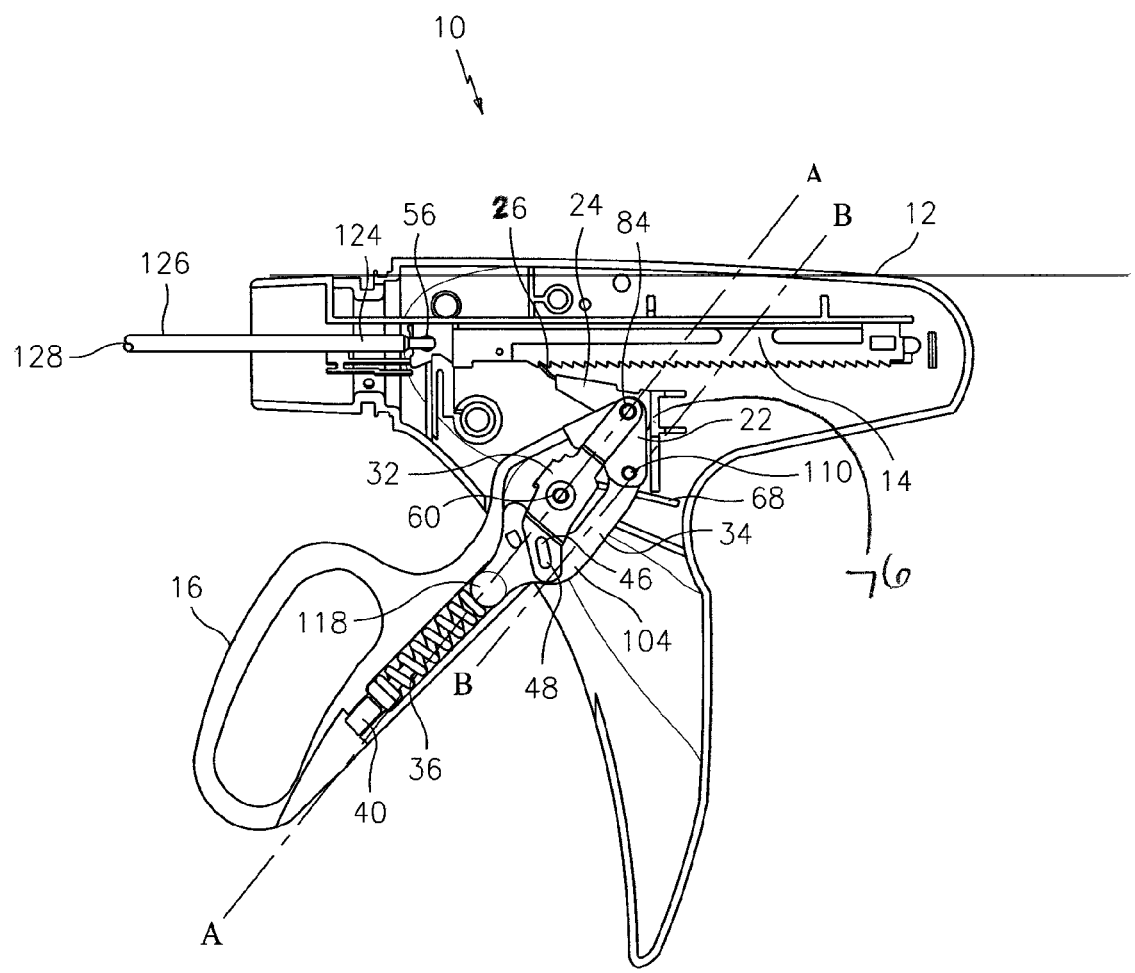
FIG. 3 is a side view of the handle assembly with half of the handle housing removed and in an initial position.

Referring now to FIGS. 3-6, and initially with regard to FIG. 3, the operation of handle assembly 10 incorporating adjustable force-limiting mechanism 30 is described. As noted above, handle assembly 10 is configured for use in various surgical instruments. Due to the adjustable nature of force-limiting mechanism 30, handle assembly 10 is particularly suitable for use in clip or staple applying surgical instruments for limiting the force applied to the clip applying mechanism, staple applying mechanism, jaw moving mechanism, etc. In the initial position, trigger 16 is biased to an open position by torsion spring 68 relative to handle assembly 12. Pawl 24 hits wall 76 so that pawl 24 is disengaged from rack 14. When assembled to a clip or staple applying distal end of portion, a firing rod 126 of the clip or staple applying distal end is mounted to handle assembly 10. Specifically, a proximal end 124 of firing rod 126 may be mounted within socket 56 on rack 14. A distal end of 128 of firing rod 126 extends to clip or staple applying and feeding mechanisms associated with the clip applying distal and portion of the surgical instrument.

As shown, in the initial position, an axis A-A is defined through mounting post 60 and pin 84 connecting upper carrier 22 to lower carrier 32. A second axis B-B is defined generally through connecting rod 34 and pin 110 joining connecting rod 34 to upper carrier 22. It should be noted that connecting rod 34 may pivot relative to upper carrier 22 about pin 110. Spring 36 exerts pressure against ball end 118 of connecting rod 34. As noted above, prior to use, a surgeon or manufacturer may preset the "break away force" by use of adjustment screw 40. In the operative condition, at least one protrusion 48 on connecting rod 34 is firmly seated within slots 46 in lower arm 104 of lower carrier 32. In typical operation, movement of handle 16 relative to handle assembly 12 causes lower carrier 32, connecting rod 34 and upper carrier 22 to pivot about mounting post 60 as a single connected unit. Pivoting of upper carrier 22 about mounting post 60 moves pawl 24 away from wall 76 so that pawl 24 pivots into engagement from rack 14. Pawl 24 is driven distally by the handle 16 to advance rack 14 distally within handle assembly 12, thereby moving firing rod 126 to actuate one or more functions associated with the distal and portion of the surgical instrument.

Figure 4:
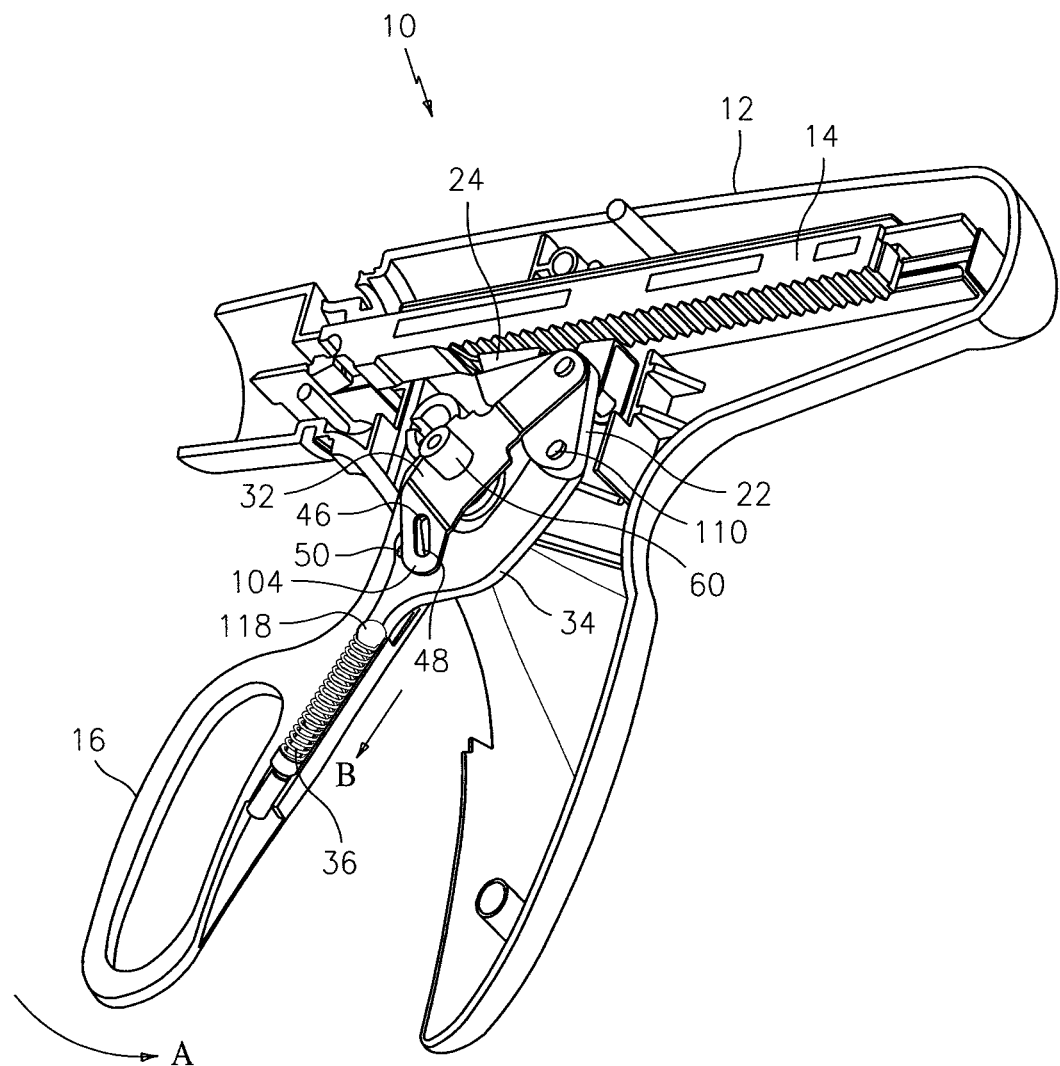
FIG. 4 is a perspective view of the handle assembly during initial deactivation of a force-limiting mechanism associated with the handle assembly.

Referring now to FIG. 4, handle assembly 10 is shown in an initial actuating condition with trigger 16 being pivoted in the direction of arrow A. When a situation occurs in the distal end portion of the associated surgical instrument such that rack 14 can no longer translate distally within handle housing 12, pawl 24 is prevented from distal movement thereby preventing upper carrier 22 and lower carrier 32 from pivoting relative to mounting post 60. In the alternative, a situation occurs where the force applied at the handle has reached a predetermined threshold.

Figure 5:
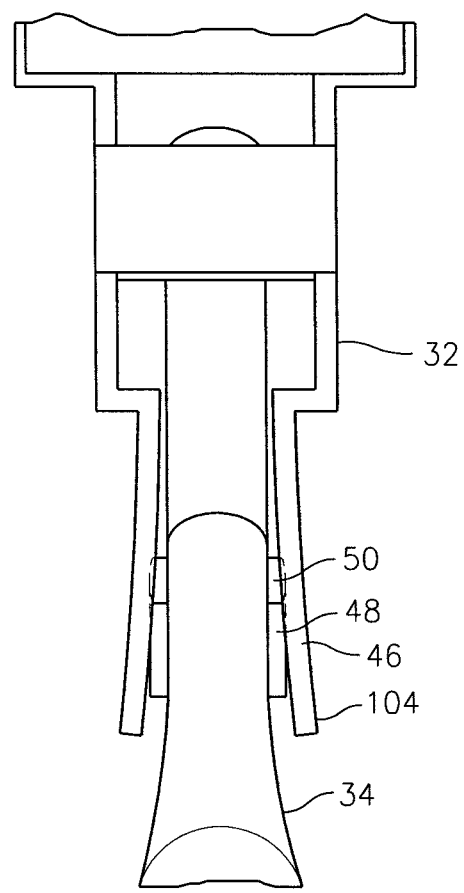
FIG. 5 is an end view of the force-limiting mechanism components of the handle assembly during disengagement of the force-limiting mechanism from an associated drive assembly.

Referring now to FIGS. 4 and 5, as continued force is exerted on trigger 16 in the direction of arrow A, connecting rod 34 attempts to continue to pivot about mounting post 60 relative to lower carrier 32. Because connecting rod 34 is pivotally fixed relative to upper carrier 22 at pin 110, connecting rod 34 is driven downwardly in the direction of arrow B against the force of spring 36. The axes A-A and B-B shown in FIG. 3 begin to rotate with respect to each other. Movement of connecting rod 34 downwardly relative to carrier 32 forces lower arms 104 to flex or splay outwardly such that slots 46 lift away from protrusions 48 in connecting rod 34. With the slots 46 disconnected from protrusions 48, the connecting rod 34 can pivot with respect to lower carrier 32. When protrusions 48 have become completely disconnected from slots 46 in lower arms 104, connecting rod 34 is disconnected from lower carrier 32. Trigger 16 can continue to pivot to a fully closed position as best shown in FIG. 6.

Figure 6:
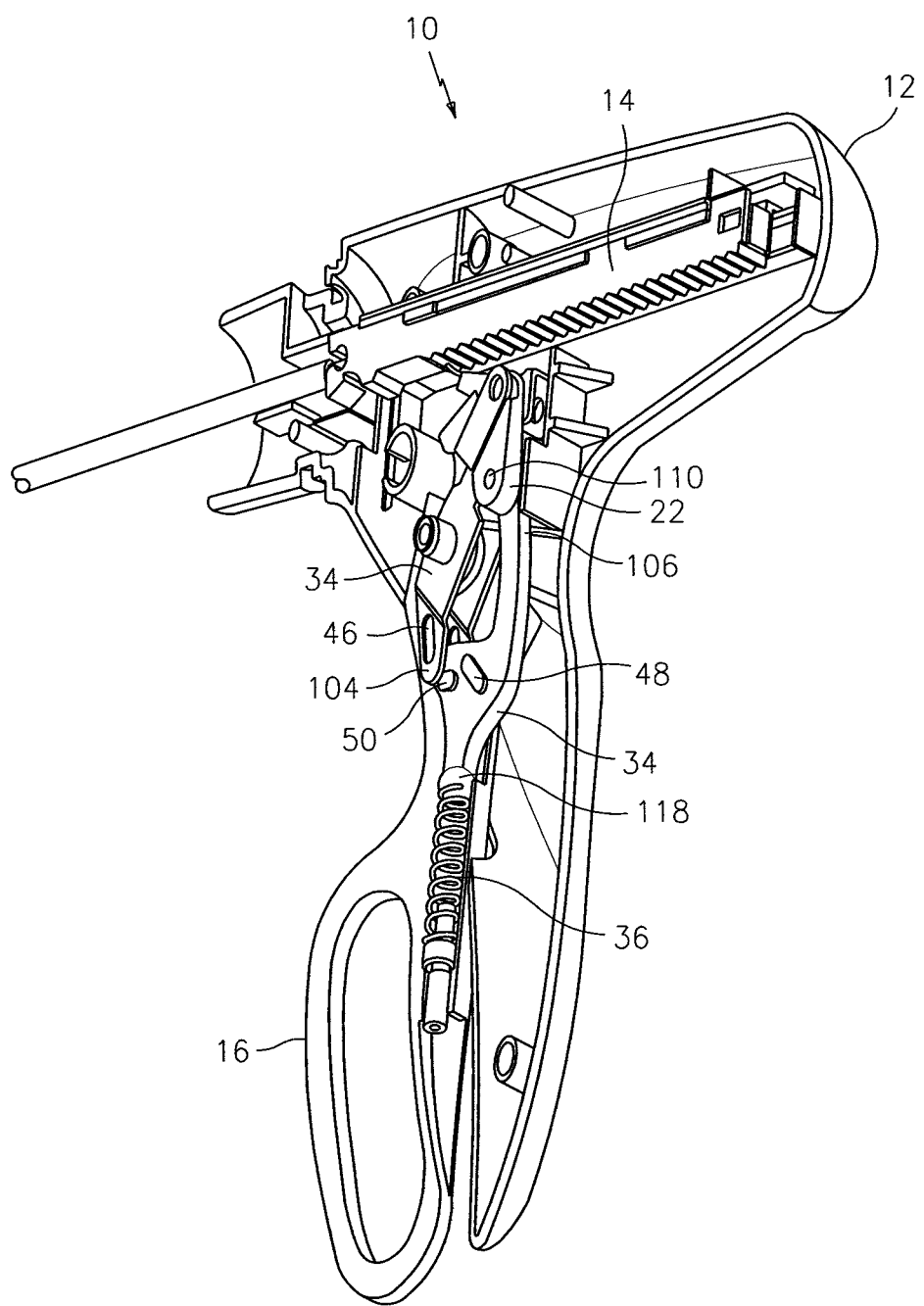
FIG. 6 is a perspective view of the handle assembly with the force-limiting mechanism components disconnected from the drive assembly.
Figure 7:
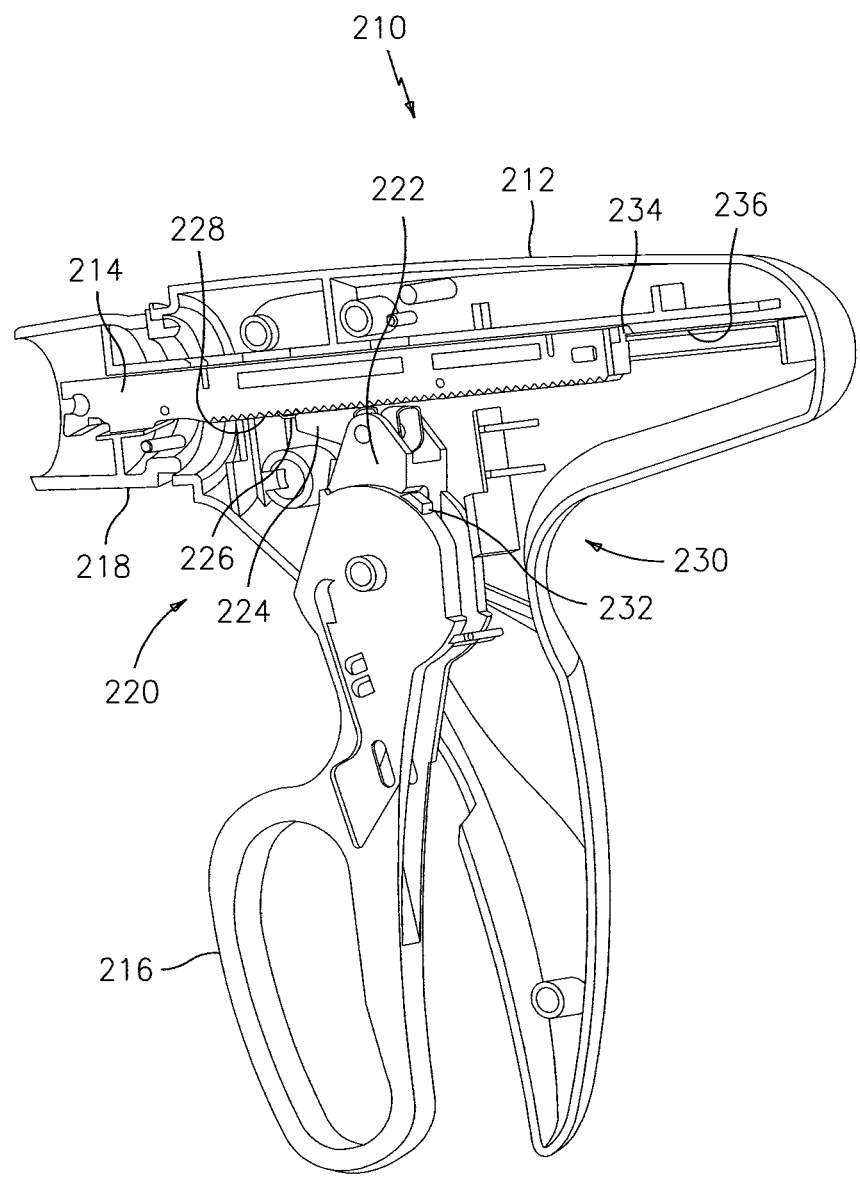
FIG. 7 is a perspective view of a handle assembly incorporating a force-limiting trigger switch, with half of a handle housing removed.

As shown in FIG. 6, lower arms 104 are maintained in a flex outwardly condition relative to connecting rod 34 by the presence of ramps 50 on connecting rod 34. Once the force encountered by force-limiting mechanism 32 decreases from the "break away force," trigger 16 may be returned to an open position due to the bias of torsion spring 68 and/or spring 36. As trigger 16 returns to the open position, lower arms 104, which have been maintained in a flex outwardly condition by ramps 50, are allowed to reset over connecting rod 34 such that slots 46 reengage protrusions 48 on connecting rod 34. This movement returns handle assembly 10 back to the initial operating position as shown in FIG. 3.

Thus, it can be seen that handle assembly 10 incorporating adjustable force-limiting mechanism 30 can safely be used to actuate distal end portions of the surgical instrument while preventing the distal end of the instrument from exceeding excessive forces (i.e. the "break away force") on tissue and/or instrument parts, and thereby prevent damage to tissues and the instrument itself.

Now referring to FIGS. 7-12, there is disclosed a handle assembly 210 for use with a surgical instrument. Handle assembly 210 incorporates a force-limiting mechanism 230 to prevent excessive force applied to tissue and to prevent damage to handle assembly 210 in the event of an overload condition present at an associated end effector. Handle assembly 210 generally includes a handle housing 212 enclosing an elongated driving rack 214 mounted for longitudinal movement within handle housing 212. While handle assembly 210 is illustrated with only one half of handle housing 212 visible, one skilled in the art will appreciate that a complete and fully functional handle assembly 210 will include both halves of handle housing 212. Handle assembly 210 additionally includes a trigger 216 movably mounted on handle housing 212. Actuation of trigger 216 causes driving rack 214 to move longitudinally within handle housing 212.

Handle housing 212 is additionally provided with a journaled nose portion 218 for rotatable support of the distal end portion of a surgical instrument. This allows end effectors associated with the distal end portion of the surgical instrument to be rotated relative to handle assembly 210.

To move driving rack 214, handle assembly 210 includes a drive assembly 220 positioned between driving rack 214 and trigger 216. Drive assembly 220 transfers motion applied to trigger 216 by an operator's hand to driving rack 214 to translate driving rack 214 longitudinally within handle housing 212 and thus actuate an associated end effector. Drive assembly 220 includes a carriage 222 which is mounted for movement along with trigger 216. A pawl 224 is pivotally connected to carriage 222 and is provided to engage driving rack 214 to move driving rack 214 within handle housing 212. Specifically, pawl 224 is provided with a distal lip 226 which is configured to engage teeth 228 provided on driving rack 214. Pawl 224 is spring biased into engagement with driving rack 214. As noted hereinbelow, teeth 228 are oriented such that distal lip 226 can engage teeth 228 and move driving rack 214 distally within handle housing 212 when pawl 224 is moved in the distal direction and disengage from driving rack 214 as pawl 224 is drawn in a proximal direction relative to driving rack 214.

As noted hereinabove, handle assembly 210 includes a force-limiting mechanism 230 which is provided to disengage trigger 216 from drive assembly 220, and thus from driving rack 214, when force-limiting mechanism 230 encounters a predetermined amount of force present between drive assembly 220 and trigger 216. This may occur in a situation where an end effector encounters sufficiently stiff or tough materials such that continued actuation of the surgical instrument will result in damage to the surgical instrument or to tissue. Additionally, the excessive force condition may occur in the event of damage to the associated end effector thereby preventing driving rack 214 from translating longitudinally within handle housing 212.

In a particular application, the excessive force condition can be preset during configuration of handle assembly 210 such that an end effector associated with handle assembly 210 may only apply a force up to a predetermined force to the tissue being operated upon. Once the predetermined force has been reached, force-limiting mechanism 30 enables trigger 216 to be disengaged from drive assembly 220 thereby preventing an excessive amount of force being applied to tissue.

Force-limiting mechanism 230 includes a plunger 232 which is movably mounted on trigger 216. Plunger 232 is configured to engage carriage 222 and transfer the motion of trigger 216 to carriage 222, and thus to pawl 224, to translate rack 214 within handle housing 212. Force-limiting mechanism 230 operates to disengage trigger 216 from carriage 222 by disengaging plunger 232 from carriage 222 in response to a predetermined force existing between carriage 222 and plunger 232.

As noted hereinabove, rack 214 is mounted for longitudinal movement within handle housing 212. Rack 214 includes a rack lip 234 which rides along a longitudinal housing rail 236 provided on handle housing 212. While rack 214 is disclosed as moving along housing rail 236, other means of supporting rack 214 for longitudinal movement within handle housing 212 may alternatively be provided, such as, for example, grooves, tracks, or other methods of longitudinally supporting rack 214 for movement within handle housing 212.

Figure 8:
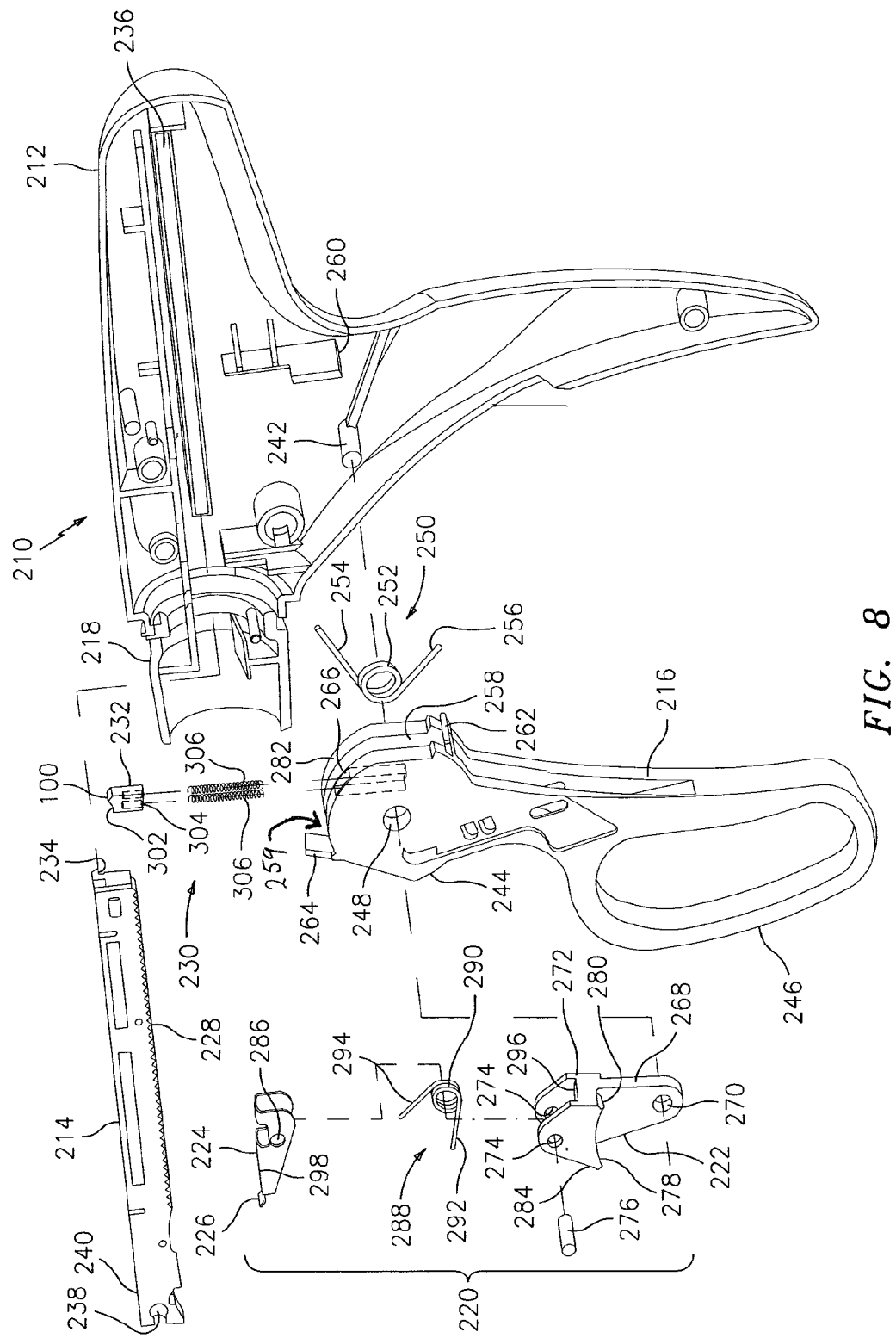
FIG. 8 is perspective view, with parts separated, of the handle assembly of FIG. 7.

Referring to FIG. 8, the components of handle assembly 210 are described in detail. As noted above, handle assembly 210 is configured for use with the distal end section of various surgical instruments which incorporate movable end effectors. Rack 214 of handle assembly 210 is provided with a socket 238 formed on a distal end 240 of rack 214. Socket 238 may be configured to receive a driving or motion rod associated with the distal end components of a surgical instrument. While rack 214 is illustrated as having socket 238, other means of connecting rack 214 to the movable components of a distal end of a surgical instrument are also contemplated herein.

To allow trigger 216 to move relative to handle housing 212, handle housing 212 is provided with a mounting post 242 which serves as a pivot point for both trigger 216 and carriage 222 in a manner described in more detail hereinbelow. Trigger 216 is provided with a body portion 244 and an open finger portion 246 depending from body portion 244. Body portion 244 includes a pivot hole 248 which fits over mounting post 242 on handle housing 212. A torsion spring 250 is provided between handle housing 212 and trigger 216 to bias trigger 216 into a distal most or open position. Torsion spring 250 includes a central portion 252, a first arm 254 and a second arm 256. Torsion spring 250 fits within a central slot or cavity 258 formed in body portion 244 of trigger 216. Central portion 252 fits over mounting post 242 and first arm 254 rests against a housing wall 260 formed handle housing 212. Second arm 256 of torsion spring 250 engages a proximal tab 262 formed on body portion 244 to bias trigger 216 into the open position.

Body portion 244 of trigger 216 additionally includes a forward tab 264 for engagement with carriage 222 to move carriage 222 proximally relative to rack 214. Body portion 244 further includes a plunger pocket 266 for receipt of plunger 232 to allow plunger 232 to move into and out of engagement with carriage 222 in a manner described in more detail hereinbelow.

With reference to FIG. 8, carriage 222 generally includes a lower portion 268 having a mounting hole 270. Lower portion 268 fits within cavity 258 formed in trigger 216 such that mounting hole 270 fits over mounting post 242. Thus, carriage 222 pivots about a common axis with body portion 244 of trigger 216. Carriage 222 additionally includes a partially sectioned or split upper portion 272 having a pair of mounting holes 274. A pivot pin 276 is provided through mounting holes 274 to attach pawl 224 to carriage 222. This enables pawl 224 to be driven longitudinally by movement of carriage 222, as well as allowing pawl 224 to pivot relative to carriage 222.

Carriage 222 additionally includes an undercut or arcuate surface 278 so that trigger 216 may pivot relative to carriage 222 when force-limiting mechanism 230 disengages trigger 216 from carriage 222. Carriage 222 is provided with an angled surface 280 which is configured to releasably engage a corresponding surface on plunger 232 of force-limiting mechanism 230. Trigger 216 is provided with a corresponding arcuate surface 282 so that trigger 216 can pivot independently of carriage 222. Upper portion 272 of carriage 222 includes a leading edge 284 which is engaged by a front edge 259 of slot 258 so as to rotate carriage 222 clockwise, in response to release of trigger 216, and thus draw pawl 224 proximally within handle housing 212.

Pawl 224 is formed as a generally U-shaped or saddle member having a pair of mounting holes 286. Pawl 224 is pivotally connected to carriage 222 by insertion of pin 276 through mounting holes 286. Drive assembly 220 additionally includes a torsion spring 288 for biasing pawl 224 into engagement with rack 214. Specifically, torsion spring 288 includes a central portion 290, a first arm 292 and a second arm 294. Central portion 290 fits over and is supported by pin 276 and first arm 292 rests against a surface 296 formed on carriage 222. Second arm 294 engages an underside pawl surface 298 of pawl 224 to bias pawl 224 upward into engagement with rack 214.

As noted hereinabove, handle assembly 210 incorporates a force-limiting mechanism 230 which enables trigger 216 to be disengaged from drive assembly 220 when drive assembly 220 is prevented from moving due to factors including the inability of rack 214 to move. Force-limiting mechanism 230 generally includes plunger 232 and a pair of springs 306, which are located within plunger pocket 266 and beneath plunger 232, to bias plunger 232 upwardly into engagement with carriage 222.

Figure 10:
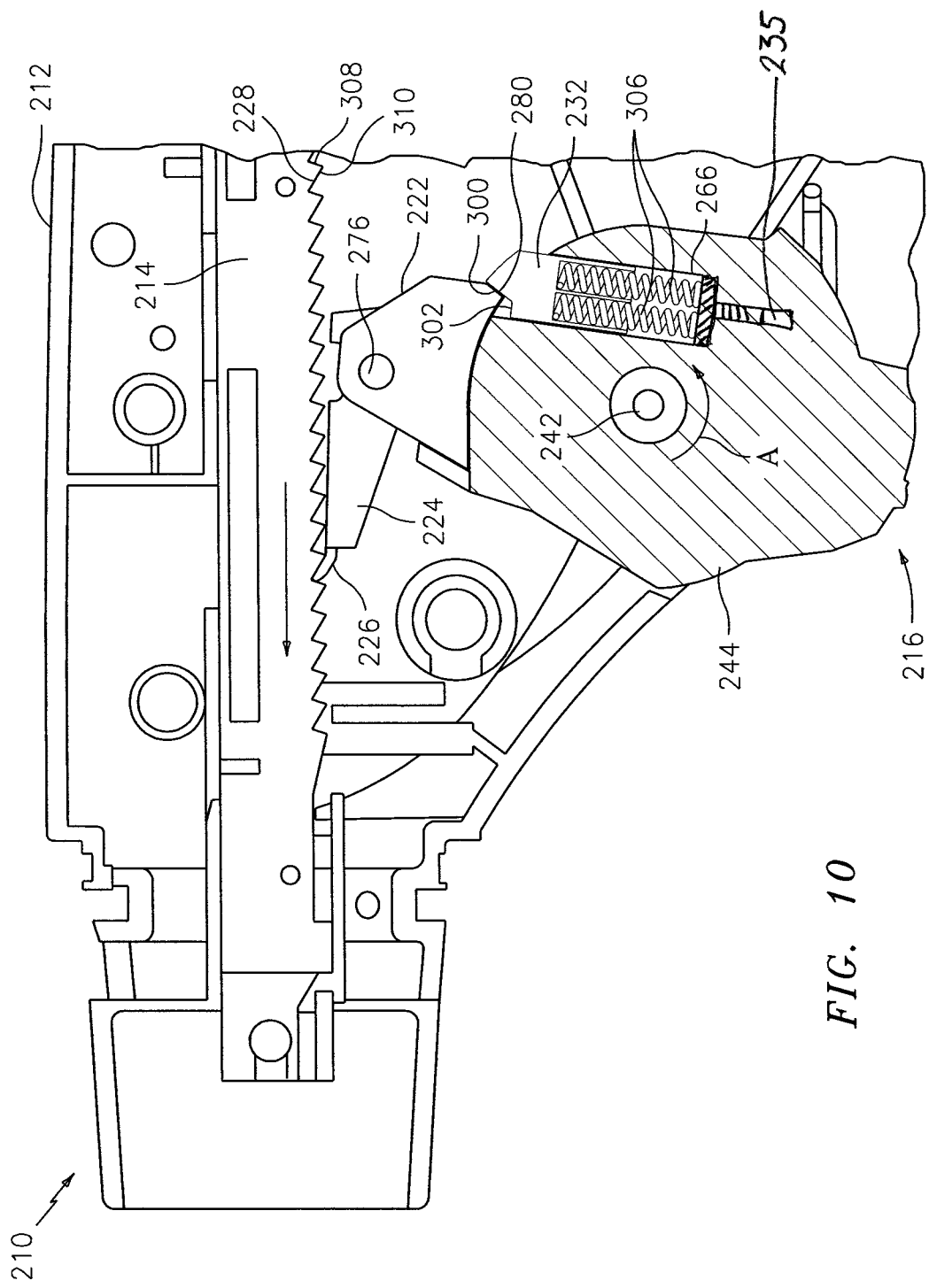
FIG. 10 is an enlarged side view of the handle assembly in an initial, actuated condition.

With reference to FIG. 10, plunger 232 includes an angled surface 300 which is configured to engage angled face 280 on carriage 222. Engagement of angled surface 300 with angled face 280 allows trigger 216 to be connected to carriage 222 and pivot carriage 222 as trigger 216 is actuated. As shown, plunger 232 additionally includes a relatively flat surface 302 which rests against arcuate surface 278 of carriage 222 and prevents plunger 232 from springing out of plunger pocket 266 and trigger 216. In one embodiment, plunger 232 is formed with a plunger pocket 304 (FIG. 8) for receipt of a portion of springs 306.

The amount of force encountered by plunger 232 such that plunger 232 disconnects from carriage 222 may be preset in at least two different ways. First, angled face 280 and angled surface 300 may be formed to define a predetermined coefficient of friction therebetween. This will, in part, determine the amount of force necessary for angled surface 300 to slip relative to angled face 280 and allow plunger 232 to be forced downwardly within plunger pocket 266 and disengage from carriage 222. Second, the force of springs 306 may be chosen to determine the force necessary to urge plunger 232 downwardly within plunger pocket 266 and thereby disengage plunger 232 from carriage 222. The angle of angled surface 300 and angled face 280 can be chosen to affect the predetermined amount of force. It should be noted that, while force-limiting mechanism 230 is illustrated as utilizing two springs 306, any number of springs, as well as other forms of springs, may be utilized to urge plunger 232 into engagement with carriage 222. Third, an adjustment spring 235 (FIG. 10) may be included to facilitate adjustment of spring force.

Figure 9:
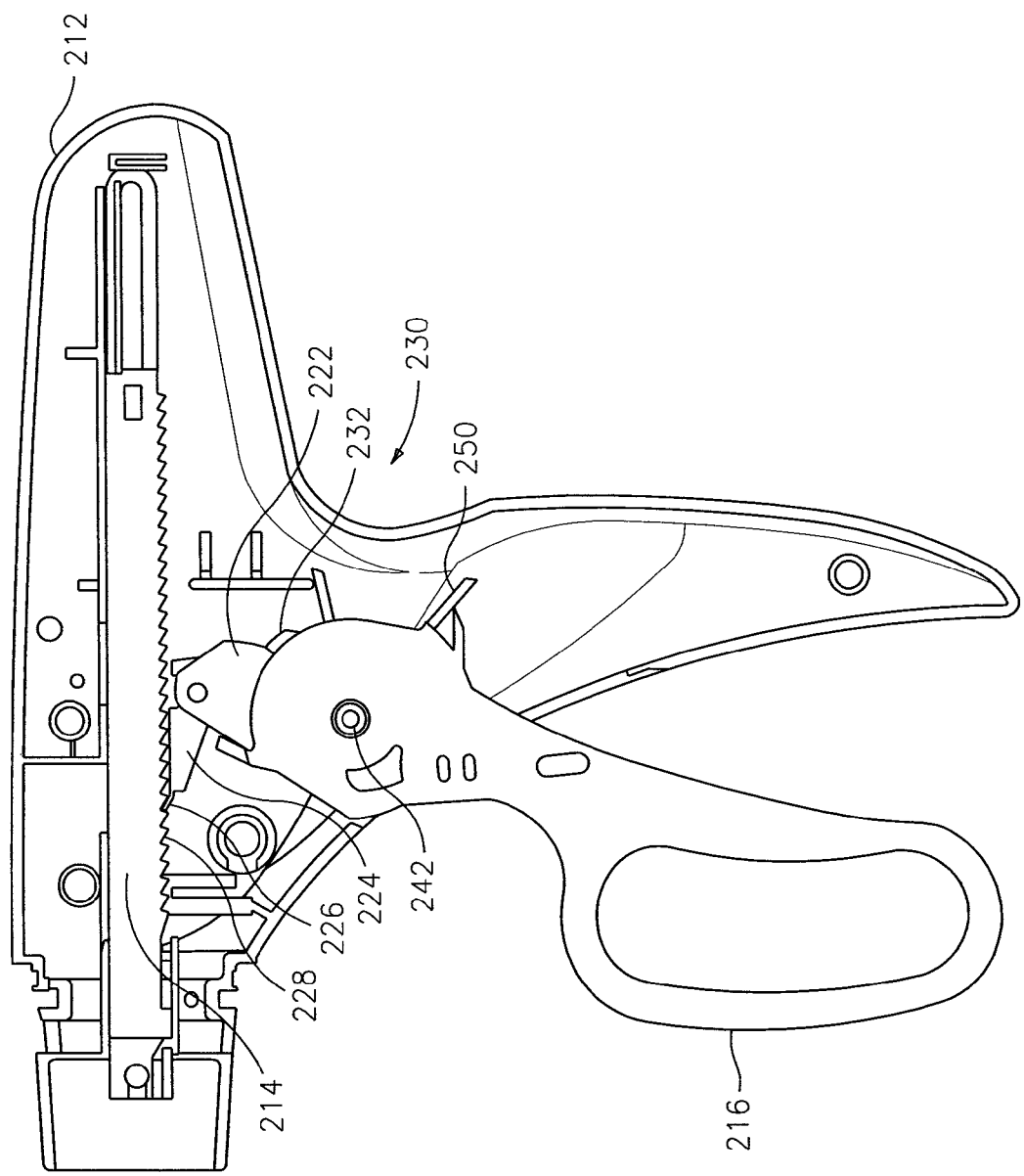
FIG. 9 is side view of the handle assembly, with half of the handle housing removed, in an initial, pre-firing condition.

Referring now to FIGS. 9-12, and initially with respect to FIG. 9, the operation of handle assembly 210 to advance to rack 214 within handle housing 212 is described. As shown, in an initial position, rack 214 is in a proximal most position within handle housing 212 and trigger 216 is biased to an open or distal most position by torsion spring 250. Plunger 232 of force-limiting mechanism 230 is engaged with carriage 222 allowing carriage 222 to pivot about common axis on mounting post 242 with trigger 216. Pawl 224 is urged upwardly due to the bias of torsion spring 288 (FIG. 8) urging distal lip 226 of pawl 224 into engagement with teeth 228 of rack 214.

Referring now to FIG. 10, as trigger 216 is squeezed or moved proximally relative to handle housing 212, body portion 244 of trigger 216 rotates in a counterclockwise fashion about mounting post 242. Carriage 222 pivots commonly about mounting post 242 with body portion 244. As noted hereinabove, angled face 280 of carriage 222 is in engagement with angled surface 300 of plunger 232 maintaining the connection between carriage 222 and trigger 216. As carriage 222 pivots about mounting post 242, it drives pawl 224 distally thereby driving rack 214 distally in response to the engagement of distal lip 226 with teeth 228.

As is common with rack and pawl engagement systems, rack teeth 228 include relatively flat driving surfaces 308 which are configured to be engaged with distal lip 226 of pawl 224 so that pawl 224 can drive rack 214 longitudinally. Rack teeth 228 additionally include angled or sloped surfaces 310. Sloped surfaces 310 allow pawl 224 to moved proximally relative to rack 214 such that distal lip 226 rides over angled surfaces 310 and moves downwardly against the bias of torsion spring 288. This allows pawl 224 to be drawn proximally back to a new position so that trigger 216 may be actuated to again drive rack 214 a farther amount distally.

Figure 11:
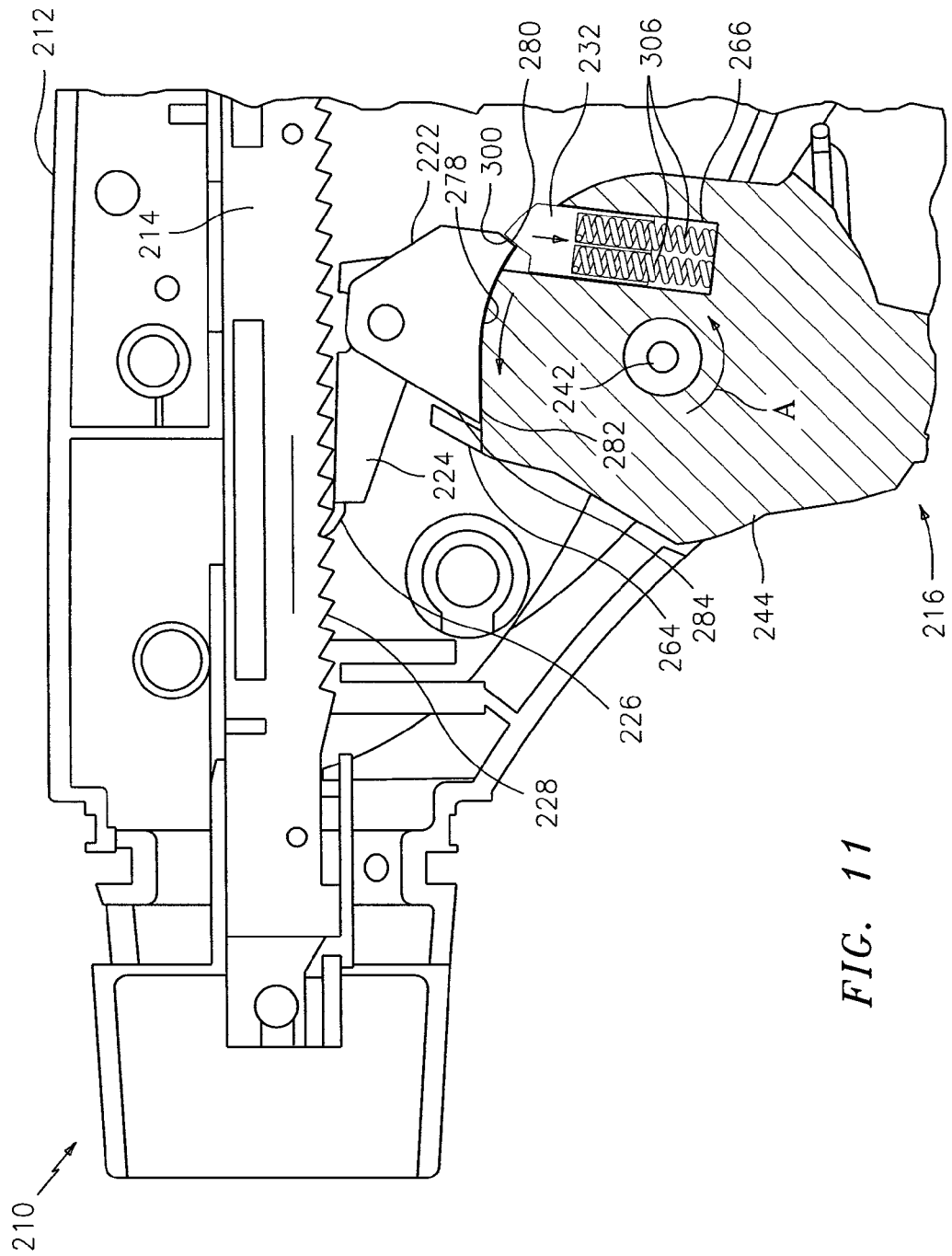
FIG. 11 is an enlarged side view of the handle assembly during initial actuation and encountering an overload condition.

Referring now to FIG. 11, as noted hereinabove, handle assembly 210 is provided with force-limiting mechanism 230 which prevents damage to tissue due to excessive forces applied to the tissue by an end effector associated with handle assembly 210, as well as preventing damage to handle assembly 210 and an associated end effector in the event components of the surgical instrument become damaged during use. This occurs when rack 214 encounters excessive resistance against distal motion within handle housing 212. When this occurs, the resistance force encountered by a rack 214 is transmitted through pawl 224 to carriage 222. When the resistance encountered by carriage 222 rises to a predetermined amount, angled surface 300 of plunger 232 begins to slip relative to angled face 280 of carriage 222. Plunger 232 is forced downwardly within plunger pocket 266 against the bias of springs 306. As noted hereinabove, the force necessary to move plunger 232 downwardly within pocket 166 is determined by the coefficient of friction present between angled face 280 of carriage 222, the component of the friction force acting generally downwardly against the spring or springs 306, and angled surface 300 of plunger 232 and the predetermined resistance force present in springs 306. As shown, as plunger 232 moves downwardly within plunger pocket 266, body portion 244 of trigger 216 continues to rotate counterclockwise causing forward tab 264 of body portion 244 to separate from leading edge 284 of carriage 222. Because arcuate surface 278 of carriage 222 has approximately the same radius as arcuate surface 282 of body portion 244, trigger 216 may continue to pivot about mounting post 242 while carriage 222 remains stationary. Handle assembly 210 may include a stop or other mechanism for maintaining the position of rack 214 when force-limiting mechanism 230 releases trigger 216.

Figure 12:
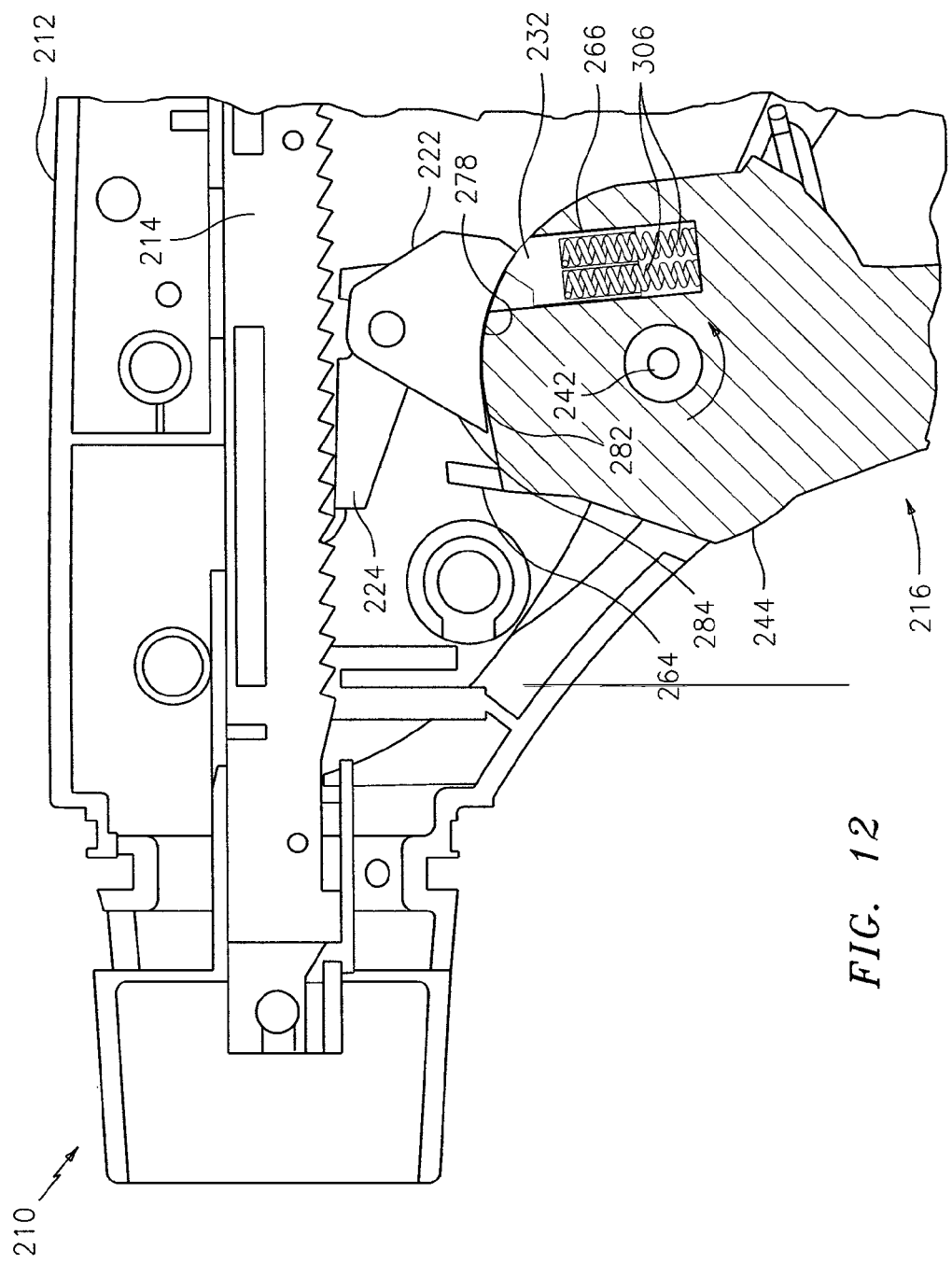
FIG. 12 is an enlarged side view of the handle assembly during an overload condition with a trigger disengaged from drive components of the handle assembly.

As best shown in FIG. 12, once plunger 232 has moved completely downwardly within plunger pocket 266, plunger 232 is disconnected from carriage 222, thus allowing body portion 244 of trigger 216 to freely rotate without imparting any force to carriage 222, and thus to pawl 224 and rack 214. While not specifically shown in this embodiment, upon release of trigger 216 against the bias of torsion spring 250 (FIG. 8) body portion 244 will rotate clockwise bringing forward slot 254 of body portion 244 into engagement with leading edge 284 of carriage 222. This allows trigger 216 to drive carriage 222, and thus pawl 224, proximally relative to rack 214 to reset for further actuation of trigger 216.

In this manner, force-limiting mechanism 230 allows handle assembly 210 to be actuated and operate an associated distal end effector without damage to tissue or the internal components of a surgical instrument consisting of handle assembly 210 and an associated distal end portion. By choosing the appropriate strength for springs 306 and/or designing the predetermined coefficient of friction and angle for angled face 280 and angled surface 300, the maximum force applied to tissue, as well as the internal components of handle assembly 210, can be predetermined.

It will be understood that various modifications may be made to the embodiment disclosed herein. For example, different types of springs may be substituted for the coil springs illustrated to bias the disclose clutch mechanism into the drive assembly. Further, the composition and orientation of the disclose clutch components may be altered to engage the drive assembly in differing manners. Additionally, the disclosed drive assembly need not necessarily include a rack and pawl system but may be substituted for other drive systems such as, for example, gears, motor-driven systems, etc. The force-limiting mechanism may include an adjustment mechanism for adjusting the threshold force for the force-limiting mechanism. The force-limiting mechanism may be provided in handle assemblies for graspers, clip appliers, staplers, surgical instruments for applying energy to tissue, or other instruments. Therefore, the above description should not be construed as limiting, but merely as exemplifications of a particular embodiment. Those skilled in the art will envision other modifications within the scope and spirit of the claims appended hereto.

The invention claimed is:

1. A handle assembly for use with a surgical instrument having an operative distal end portion comprising:
   a handle housing;
   a drive element movably mounted within the handle housing and connected to an operative distal end portion for performing surgery;
   an actuator movably mounted on the handle housing; and
   a force-limiting mechanism disposed between the drive element and the actuator, the force-limiting mechanism having a breakaway force, the force-limiting mechanism including:
      a carriage in mechanical cooperation with the actuator;
      a pawl pivotably connected to the carriage;
      a plunger slidably connected to the actuator;
         wherein the carriage includes an angled surface for engaging at least a portion of the plunger;
      the force-limiting mechanism being attached to the actuator so that the force-limiting mechanism moves with the actuator when the force applied to the actuator is less than the breakaway force and so that the force-limiting mechanism pivots with respect to the actuator when the force applied to the actuator meets the breakaway force, the force-limiting mechanism applying a drive force to the drive element when the force applied to the actuator is less than the breakaway force.

2. The handle assembly as recited in claim 1, wherein the force-limiting mechanism includes a lower carrier.

3. The handle assembly as recited in claim 2, wherein the force-limiting mechanism includes a connecting rod connected to the actuator and releasably connected to the lower carrier.

4. The handle assembly as recited in claim 3, wherein the connecting rod is slidably disposed in the actuator and a spring is positioned between the actuator and the connecting rod.

5. The handle assembly as recited in claim 4, wherein the lower carrier is pivotably connected to the actuator.

6. The handle assembly as recited in claim 5, wherein the lower carrier is pivotably connected to an upper carrier, the upper carrier being pivotably connected to the connecting rod.

7. The handle assembly as recited in claim 2, wherein the drive element comprises a rack having at least one tooth and further comprising a pawl pivotably connected to the force-limiting mechanism for engagement with the rack.

8. The handle assembly as recited in claim 1, wherein the plunger is slidably disposed at least partially within the actuator.

9. The handle assembly as recited in claim 8, wherein at least one spring is disposed between the plunger and the actuator.

10. The handle assembly as recited in claim 1, wherein the plunger includes an angled face for engaging the angled surface, the angled surface and angled face being arranged so that the carriage is able to depress the plunger.

11. The handle assembly as recited in claim 10, wherein the plunger is biased toward the carriage with a predetermined amount of force.

* * * * *